US006075178A

United States Patent [19]
La Wilhelm et al.

[11] Patent Number: 6,075,178
[45] Date of Patent: Jun. 13, 2000

[54] ABSORBENT ARTICLE WITH WETNESS INDICATOR

[75] Inventors: Hoa La Wilhelm, Appleton, Wis.; Jennifer Marie Bauerle, Hull, United Kingdom; David Willis Heyn, Neenah, Wis.; Allen Todd Leak, Neenah, Wis.; Dale Arthur Peterson, Neenah, Wis.; Carl Gerard Rippl, Appleton, Wis.; Diane Michele Underhill, Neenah, Wis.; Jerome James Workman, Jr., Appleton, Wis.

[73] Assignee: Kimberly-Clark Worldwide, Inc., Neenah, Wis.

[21] Appl. No.: 09/097,905

[22] Filed: Jun. 16, 1998

Related U.S. Application Data

[60] Provisional application No. 60/060,366, Sep. 29, 1997.

[51] Int. Cl.$^7$ .................................................. A61F 13/15
[52] U.S. Cl. ...................... 604/361; 604/358; 604/385.1; 604/385.2
[58] Field of Search ............................... 604/361, 385.1, 604/358, 385.2

[56] References Cited

U.S. PATENT DOCUMENTS

| | | | |
|---|---|---|---|
| 3,675,654 | 7/1972 | Baker et al. | 128/287 |
| 3,794,024 | 2/1974 | Kokx et al. | 128/285 |
| 3,901,236 | 8/1975 | Assarsson et al. | 128/284 |

(List continued on next page.)

FOREIGN PATENT DOCUMENTS

| | | | |
|---|---|---|---|
| 0 148 115 A1 | 7/1985 | European Pat. Off. | A41B 13/02 |
| 0 217 032 A2 | 4/1987 | European Pat. Off. | D04H 13/00 |
| 0 452 727 B1 | 10/1991 | European Pat. Off. | D04H 13/00 |

(List continued on next page.)

OTHER PUBLICATIONS

Derwent World Patent Database abstract of EP 148115: Description of R. Levy, "Baby's Napkin With Urine Indicator."

(List continued on next page.)

*Primary Examiner*—John G. Weiss
*Assistant Examiner*—Miley Craig Peppers, III
*Attorney, Agent, or Firm*—Paul Yee

[57] ABSTRACT

An absorbent article (10) has a front waistband portion (14), a back waistband portion (12) and an intermediate portion (16). The article comprises a flexible backsheet member (30), and a liquid permeable topsheet layer (28). An absorbent body structure (32), with a retention portion (48), is sandwiched between the backsheet member (30) and the topsheet layer (28), and a wetness indicator (40) visually shows a presence of liquid in selected areas of the article. The wetness indicator is provided by at least one indicator section of the backsheet member (30) which includes a polymer sheet layer (96). Desirably, The wetness indicator is provided by at least one indicator section of the backsheet member (30) which includes a backsheet laminate material having a fibrous nonwoven web (94) attached to a polymer sheet layer (96). The indicator section of the backsheet member (30) includes a plurality of translucent windows (98) which are arranged in an area pattern and are formed by a selected thermal treatment of the polymer sheet layer (96). In particular arrangements, the translucent windows (98) can be arranged in an area pattern and can be formed by a bonding of the fibrous nonwoven web (94) to the polymer sheet layer (96) in the backsheet laminate material. A layer of contrast material (44) may be attached to the article at an operative location which is interposed between an intended wearer of the article and the indicator section of the backsheet member (30). In particular arrangements, the contrast layer (44) can have a first appearance through the translucent windows (98) when the contrast material is dry, and can have a visually different second appearance through the translucent windows (98) when the contrast material is wetted with water or other aqueous liquid.

33 Claims, 12 Drawing Sheets

U.S. PATENT DOCUMENTS

| | | | |
|---|---|---|---|
| 4,022,211 | 5/1977 | Timmons et al. | 128/287 |
| 4,076,663 | 2/1978 | Masuda et al. | 260/17.4 GC |
| 4,192,311 | 3/1980 | Felfoldi | 128/287 |
| 4,231,370 | 11/1980 | Mroz et al. | 128/287 |
| 4,286,082 | 8/1981 | Tsubakimoto et al. | 526/240 |
| 4,333,979 | 6/1982 | Sciaraffa et al. | 428/179 |
| 4,663,220 | 5/1987 | Wisneski et al. | 428/221 |
| 4,699,823 | 10/1987 | Kellenberger et al. | 428/219 |
| 4,704,116 | 11/1987 | Enloe | 604/385 A |
| 4,705,513 | 11/1987 | Sheldon et al. | 604/361 |
| 4,725,473 | 2/1988 | Van Gompel et al. | 428/156 |
| 4,741,941 | 5/1988 | Englebert et al. | 428/71 |
| 4,753,646 | 6/1988 | Enloe | 604/385 R |
| 4,916,005 | 4/1990 | Lippert et al. | 428/192 |
| 4,938,753 | 7/1990 | Van Gompel et al. | 604/385.2 |
| 5,019,073 | 5/1991 | Roessler et al. | 604/391 |
| 5,032,122 | 7/1991 | Noel et al. | 604/391 |
| 5,078,708 | 1/1992 | Haque | 604/361 |
| 5,226,992 | 7/1993 | Morman | 156/62.4 |
| 5,399,219 | 3/1995 | Roessler et al. | 156/259 |
| 5,486,166 | 1/1996 | Bishop et al. | 604/366 |
| 5,490,846 | 2/1996 | Ellis et al. | 604/366 |
| 5,540,796 | 7/1996 | Fries | 156/164 |
| 5,562,650 | 10/1996 | Everett et al. | 604/378 |
| 5,595,618 | 1/1997 | Fries et al. | 156/164 |
| 5,599,420 | 2/1997 | Yeo et al. | 156/290 |
| 5,605,735 | 2/1997 | Zehner et al. | 428/100 |
| 5,615,460 | 4/1997 | Weirich et al. | 24/446 |
| 5,624,429 | 4/1997 | Long et al. | 604/391 |
| 5,690,624 | 11/1997 | Sasaki et al. | 604/361 |
| 5,695,868 | 12/1997 | McCormack | 428/283 |
| 5,897,541 | 4/1999 | Uitenbroek et al. | 604/358 |

FOREIGN PATENT DOCUMENTS

| | | | |
|---|---|---|---|
| 0 604 731 A1 | 7/1994 | European Pat. Off. | B32B 31/00 |
| 0 738 505 A1 | 10/1996 | European Pat. Off. | A61F 13/15 |
| 0 776 645 A1 | 6/1997 | European Pat. Off. | A61F 13/42 |
| 43 11 867 A1 | 10/1994 | Germany | B32B 27/12 |
| WO 95/16562 | 6/1995 | WIPO . | |
| WO 95/16562 A1 | 6/1995 | WIPO | B32B 5/24 |
| WO 97/48358 | 12/1997 | WIPO | A61F 13/15 |

OTHER PUBLICATIONS

Derwent World Patent Database abstract of DE 4,311,867: Description of H. Boich et al., "Impermeable Fibre Film Composite Esp. For Nappies."

Patent Cooperation Treaty Search Report from the International Search Authority, International Application No. PCT/US 98/20341 dated Feb. 1, 1999.

American Society for Testing Materials (ASTM) Designation: D 737–96, "Standard Test Method for Air Permeability of Textile Fabrics," pp. 236–240, published Apr. 1996.

American Society for Testing Materials (ASTM) Designation: D 1117–80, "Standard Test Methods of Testing Nonwoven Fabrics," pp. 240–246, published May 1980.

American Society for Testing Materials (ASTM) Designation: D 1117–97, "Standard Test Methods for Nonwoven Fabrics," pp. 311–313, published Jun. 1997.

American Society for Testing Materials (ASTM) Designation: D 1682–64 (Reapproved 1975), "Standard Test Methods for Breaking Load and Elongation of Textile Fabrics," pp. 454–459, published Oct. 1964.

American Society for Testing Materials (ASTM) Designation: D 2244–85, "Standard Test Method for Calculation Of Color Differences From Instrumentally Measured Color Coordinates," pp. 388–393, published Jan. 1986.

American Society for Testing Materials (ASTM) Designation: D 5034–95, "Standard Test Method For Breaking Strength And Elongation Of Textile Fabrics (Grab Test)," pp. 674–681, published Jul. 1995.

American Society for Testing Materials (ASTM) Designation: D 5035–90, "Standard Test Method For Breaking Force and Elongation of Textile Fabrics (Strip Force)," pp. 726–731, published May 1990.

American Society for Testing Materials (ASTM) Designation: D 5035–95, "Standard Test Method For Breaking Force and Elongation of Textile Fabrics (Strip Method)," pp. 682–688, published Jul. 1995.

American Society for Testing Materials (ASTM) Designation: D 5169–91, "Standard Test Method for Shear Strength (Dynamic Method ) of Hook and Loop Touch Fasteners," pp. 687–689, published Nov. 1991.

American Society for Testing Materials (ASTM) Designation: D 5170–91, "Standard Test Method for Peel Strength ("T" Method) of Hook and Loop Touch Fasteners," pp. 690–692, published Nov. 1991.

American Society for Testing Materials (ASTM) Designation: E 308–85, "Standard Method for Computing the Colors of Objects by Using the CIE System," pp. 181–207, published Apr. 1985.

American Society for Testing Materials (ASTM) Designation: E 313–73, "Standard Test Method for Indexes of Whiteness and Yellowness of Near–White, Opaque Materials," pp. 771–774, published Jan. 1974.

CIE Publication No. 15.2, *Colorimetry*, Second Edition, 1986, pp. 1–74.

Federal Test MEthod Standard (FTMS) No. 191A, Method 5306, "Abrasion Resistance of Cloth; Rotary Platform, Double–Head (Taber) Method," Jul. 20, 1978, 7 pages.

TAPPI Official Test Method T 543 om–94, "Bending Resistance of Paper (Gurley Type Tester)," published by the TAPPI Press, Atlanta, Georgia, pp. 1–5.

American Society for Testing Materials (ASTM) Designation: E 96–80, "Standard Test Methods for Water Vapor Transmission of Materials," pp. 742–751, published Feb. 1981.

Federal Test Method Standard (FTMS) No. 191A, Method 5514, "Water Resistance of Cloth; Low Range, Hydrostatic Pressure Method," Jul. 20, 1978, 3 pages.

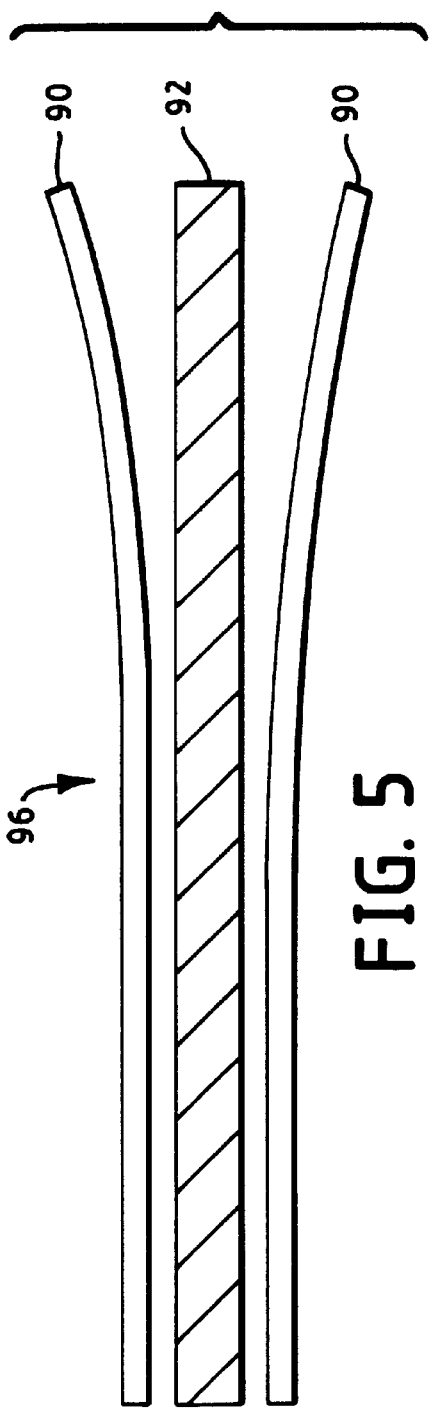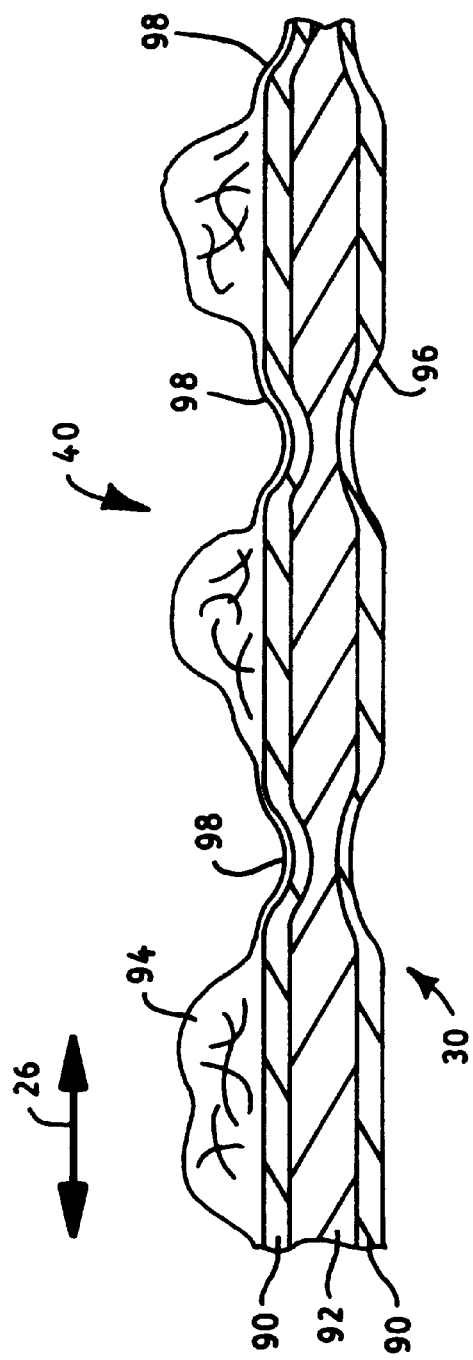

HUNTER COLOR CONTRAST RATIOS (WET VERSUS DRY) FOR SAMPLE 1 THROUGH SAMPLE 4

ABSORBENT ARTICLE WITH WETNESS INDICATOR

This application claims priority from U.S. Provisional Application Ser. No. 60/060,366 entitled "Absorbent Article with Wetness Indicator" and filed on Sep. 29, 1997, in the non of Hoa La Wilhelmetal.

FIELD OF THE INVENTION

The present invention relates to garment articles. More particularly, the present invention relates to absorbent articles, desirably disposable absorbent articles, which have an outercover distinctively configured to provide an indication of the degree of wetness within the diaper.

BACKGROUND OF THE INVENTION

Conventional garment articles, such as disposable diapers and other disposable absorbent articles, have typically employed adhesive or mechanical fasteners which attach appointed waistband sections of the articles around a wearer. In addition, various configurations of waist elastics, leg elastics, elasticized liners, and elasticized outercovers have been employed on garment articles to help produce and maintain the fit of the articles about the body contours of the wearer.

It has been desirable for a caregiver using a disposable diaper on an infant to be able to determine whether the diaper contains wetness without disturbing the infant. For example, audible alarms, have been incorporated into diapers to indicate when the diaper has been wetted.

Visual mechanisms have also been employed to signal the presence of wetness in a disposable diaper. The diapers have included printed letters or objects using specific moisture-fugitive inks or dyes placed onto the inside surface of the translucent, moisture impermeable outer cover which contacts the absorbent system. The printed objects can disappear when the wetness in the absorbent system contacts those moisture-fugitive inks or dyes.

Another visual wetness indicator has included a pH change/color change indicator material located on the inside surface of a translucent, moisture impermeable outer cover which contacts the absorbent system. The indicator material changes color upon contacting the wetness from the absorbent system.

Conventional garment articles, such as those described above, have not provided desired levels of aesthetics and comfort, and have been susceptible to excessive levels of humidity within the garment. Where the garments are configured as absorbent articles, the articles have been susceptible to excessive leakage of liquids and other waste materials. As a result, there has been a continued need for improved garments having more consistent fit, greater comfort and lower likelihood of leakage.

BRIEF DESCRIPTION OF THE INVENTION

Generally stated, the present invention provides an absorbent article having a front waistband portion, a back waistband portion and an intermediate portion. The article includes a flexible and readily conformable backsheet member, and a liquid permeable topsheet layer. An absorbent body has a retention portion and is sandwiched between the backsheet member and the topsheet layer. A wetness indicator in the article visually shows a presence of liquid in selected regions of the article. The wetness indicator includes at least one indicator section of said backsheet member which includes a backsheet material having a polymer sheet layer. The indicator section of the backsheet member also includes a plurality of translucent windows which are arranged in an area pattern and are formed by a selected thermal treatment of the polymer sheet layer. The indicator section has a first appearance when portions of the article at the translucent windows are dry, and has a visually different second appearance when portions of the article at the translucent windows are wetted with water.

In particular aspects of the invention, the indicator section can thereby provide a distinctive Contrast Ratio. For example, the Contrast Ratio can be at least about 1.1. In other aspects, a layer of contrast material can be attached to the article at an operative location which is interposed between an intended wearer of the article and the indicator section of the backsheet member. The contrast layer can have a first appearance through the translucent windows when said contrast material is dry, and has a visually different second appearance through the translucent windows when the contrast material is wetted with water.

Still another aspect of the invention can provide a distinctive article which includes a front waistband portion, a back waistband portion and an intermediate portion. The article comprises a flexible backsheet member, and a liquid permeable topsheet layer. An absorbent body structure has a retention portion and is sandwiched between the backsheet member and the topsheet layer. The article includes a wetness indicator which visually shows a presence of liquid in selected areas of the article. The wetness indicator is provided by at least one indicator section of the backsheet member which includes a backsheet laminate material having a fibrous nonwoven web attached to a polymer sheet layer. The indicator section of the backsheet member includes a plurality of translucent windows which are arranged in an area pattern and are formed by a selected thermal bonding of the fibrous nonwoven web to the polymer sheet layer in the backsheet laminate material. A layer of contrast material can be attached to the article at an operative location which is interposed between an intended wearer of the article and the indicator section of the backsheet member. The contrast layer can have a first appearance through the translucent windows when the contrast material is dry, and has a visually different second appearance through the translucent windows when the contrast material is wetted with water or other aqueous liquid.

By incorporating its various aspects, the article of present invention can provide improved comfort to the wearer. The humidity within the article can be maintained al: lower levels during the period of use, and the wetness within the article can be more efficiently monitored. A caregiver can better determine whether or not the diaper contains excessive wetness without disturbing the infant. The present invention can provide an effective, low cost, durable, easily manufactured mechanism which visually indicates to a caregiver the level of wetness within the article, without the additional manufacturing complication and consequent of applying a separate ink, dye or other expensive component to the inside of the moisture impermeable portion of the diaper outer cover. The present invention can also provide a visually and tactually pleasing, gross pattern embossment on a breathable disposable diaper outer cover to connote the aesthetic and functional properties of a durable, apparel-like fabric. In addition, the present invention can provide gross bonding pattern on the outer cover which, upon the introduction of wetness in the diaper, provides a visual indication of the wetness in a color that corresponds to the gender-design of the disposable diaper. As a result the article can be removed and changed in a more timely manner to reduce the probability of irritation to the wearer and undesired leakage.

BRIEF DESCRIPTION OF THE DRAWINGS

The present invention will be more fully understood and further advantages will become apparent when reference is made to the following detailed description of the invention and the drawings, in which:

FIG. 5 representatively shows a partially expanded, side view of a laminated polymer sheet layer or film employed with the article of the invention;

FIG. 6 representatively shows a cross-sectional, side view of a laminated and bonded backsheet member employed with the article of the invention;

DETAILED DESCRIPTION OF THE INVENTION

Figure 1:
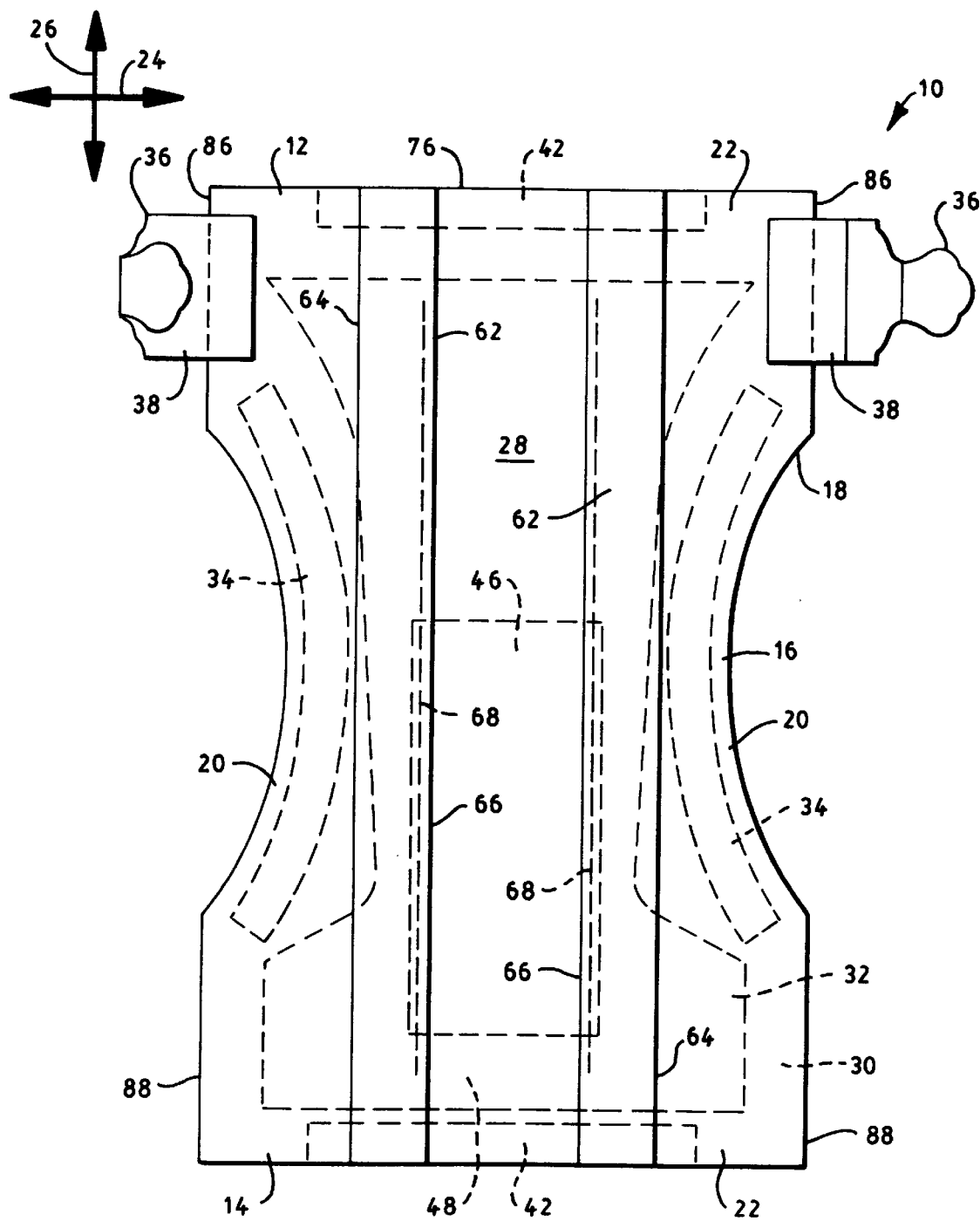
FIG. 1 shows a top, plan view of the inner, bodyside of a representative diaper article.

The various aspects and embodiments of the invention will be described in the context of a disposable absorbent article, such as a disposable diaper. It is, however, readily apparent that the present invention could also be employed with other articles, such as caps, gowns, shoe covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer. Optionally, a disposable diaper may include a single-use, absorbent insert, and a limited-use outer cover which may be reused several times. With reference to FIGS. 1, 2, 3 and 4, an article, such as the representatively shown absorbent diaper 10, has a length-wise longitudinal direction 26, a transverse lateral direction 24, and a first waistband portion 12 at the back or rear of the diaper. The first waistband portion has an inward, bodyside surface and an outward surface thereof. A second, front waistband portion 14 is positioned longitudinally opposite of the first waistband portion 12 and has an inward, bodyside surface and an outward surface thereof. An intermediate, crotch portion 16 interconnects the first and second waistband portion 12 and 14, respectively. The article comprises a flexible and conformable backsheet member 30, and a liquid permeable topsheet layer 28. An absorbent body structure 32, with a retention portion 48, is sandwiched between the backsheet member 30 and the topsheet layer 28, and a wetness indicator 40 visually shows a presence of liquid in selected areas of the article. The wetness indicator is provided by at least one indicator section of the backsheet member 30 which includes a polymer sheet layer 96. The indicator section of the backsheet member 30 has a plurality of translucent windows 98 which are arranged in a selected area pattern and are formed by a operative thermal treatment of the polymer sheet layer 96. The indicator section has a first appearance when corresponding portions of the article at the translucent windows are dry, and has a visually different second appearance when corresponding portions of the article at the translucent windows are wetted with water.

In particular aspects of the invention, the indicator section can thereby provide a distinctive Contrast Ratio. The Contrast Ratio can, for example, be at least about 1.1 or more. In other aspects, an appointed layer of contrast material 44 can be attached to the article at an operative location which is interposed between an intended wearer of the article and the indicator section of the backsheet member 30. The contrast layer 44 can have a first appearance through the translucent windows 98 when the contrast material is dry, and can have a visually different second appearance through the translucent windows 98 when the contrast material is wetted with water or other aqueous liquid.

In desired arrangements of the invention, the wetness indicator can be provided by at least one indicator section of the backsheet member 30 which includes a backsheet laminate material having a fibrous nonwoven web 94 attached to a polymer sheet layer 96. The indicator section of the backsheet member 30 includes a plurality of translucent windows 98 which are arranged in a selected area pattern and are formed by a cooperative thermal treatment of the fibrous nonwoven web 94 and the polymer sheet layer 96 in the backsheet laminate material. For example, the plurality of translucent windows 98 can be arranged in a selected area pattern and can be formed by an operative thermal treatment, such as a thermal bonding of the fibrous nonwoven web 94 to the polymer sheet layer 96 in the backsheet laminate material.

The various aspects (individually and in combination) of the present invention can advantageously help to better maintain the desired fit around the wearer. For example, the aspects of the invention can help reduce the humidity within the article and can provide improved comfort and appearance. When incorporated into the absorbent article, the various aspects of the invention can provide improved aesthetics, reduced irritation to the wearer and reduced likelihood of undesired leakage.

A desired, integral garment article of the invention can, for example, be provided by the representatively shown disposable diaper 10. The diaper can include a backsheet layer 30, a liquid permeable topsheet layer 28 connected and integrated with the backsheet layer, and an absorbent structure, such as a structure which includes absorbent body 32. The absorbent structure is sandwiched between the backsheet and topsheet layers, and is operably held laminated therebetween. A fastening system, such as a system including fasteners 36, is configured to join the back waistband portion 12 in an overlapping relation with the front waistband portion 14 to thereby encircle the wearer's body and hold the diaper secure on the wearer during use. Optionally, the fastening system can employ fastener tabs 36 which are configured to join the front waistband portion 14 in an overlapping relation with the back waistband portions 12 to thereby encircle the wearer's body during use.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article has an appointed fastener landing member 50 which is disposed on the outward surface of the article. In the example shown in FIG. 2, for example, the landing member 50 is disposed on the outward surface of the backsheet layer 30. The liquid permeable topsheet layer 28 is superposed in facing relation with the backsheet layer 30, and the absorbent body 32 is operably connected and affixed between the backsheet layer 30 and topsheet layer 28.

Figure 2:
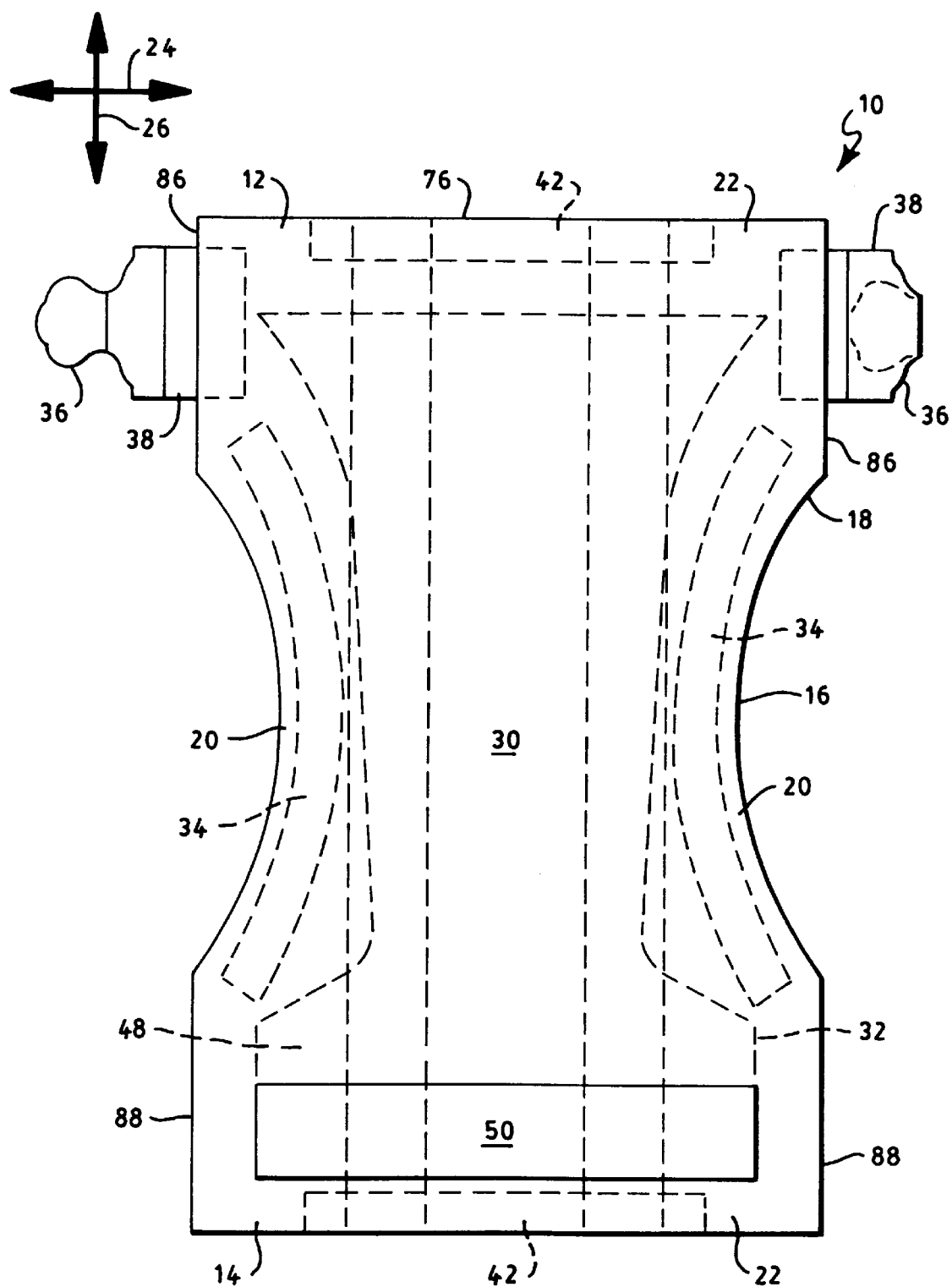
FIG. 2 shows a plan view of the outer, backsheet side of a representative diaper article.
Figure 3:
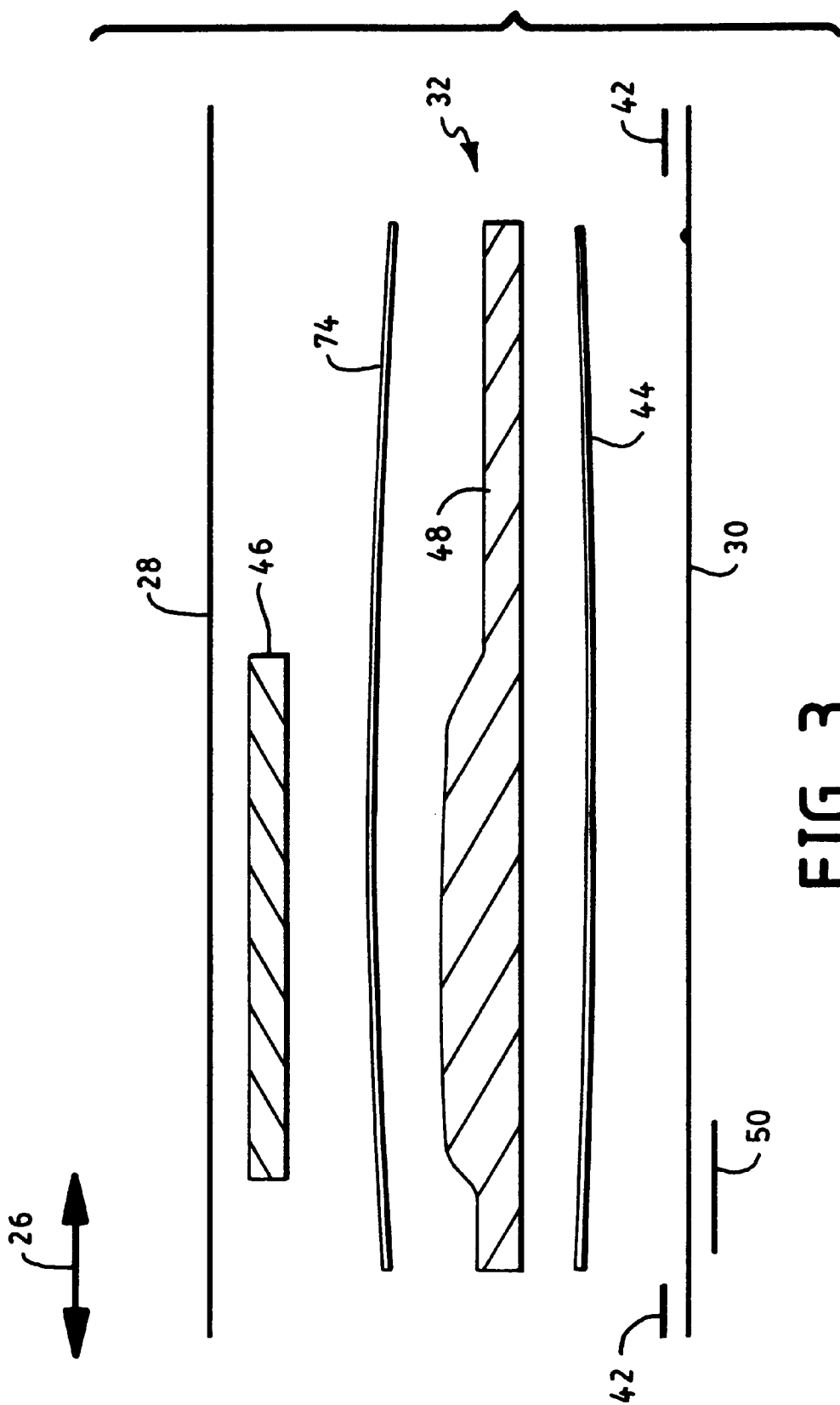
FIG. 3 representatively shows an expanded, longitudinal cross-sectional view of a diaper article of the invention.

FIGS. 1 and 2 show typical plan views of the representative disposable diaper 10 in its generally flat-out, uncontracted state (i.e., with substantially all elastic induced gathering and contraction removed). Portions of the structure are partially cut away to more clearly show the interior construction of the diaper article, and the bodyside surface of the diaper which contacts the wearer is facing the viewer. The outer edges of the diaper define a periphery 18 with longitudinally extending side edge margins 20 and laterally extending end edge margins 22. The side edges define leg openings for the diaper, and optionally, are curvilinear and contoured. The end edges are shown as straight, but optionally, may be curvilinear.

With regard to the designated surfaces of the article and components, the various inward surfaces are configured to face toward the body of the wearer when the article is placed about the wearer. The various outward surfaces are configured to face away from the wearer's body when the article is placed about the wearer.

The diaper 10 typically includes a porous, liquid permeable topsheet 28; a substantially liquid impermeable backsheet 30; an absorbent structure 32 positioned and connected between the topsheet and backsheet; a surge management portion 46 located adjacent the absorbent structure; and a system of elastomeric gathering members, such as a system including leg elastics 34 and waist elastics 42. The surge management portion is positioned in a liquid communication with a retention portion 48 of the absorbent structure, and the topsheet 28, backsheet 30, absorbent structure 32, surge management portion 46 and elastic members 34 and 42 may be assembled together into a variety of well-known diaper configurations. The diaper can additionally include a system of containment flaps 62, and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993 (attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 (attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (attorney docket No. 11,169) which issued as U.S. Pat. No. 5,540,796; and in U.S. patent application Ser. No. 08/415,383 of D. Fries, entitled AN ASSEMBLY PROCESS FOR A LAMINATED TAPE and filed Apr. 3, 1995 (attorney docket No. 11,950) which issued as U.S. Pat. No. 5,595,618. The disclosures of the above-described documents are incorporated herein by reference in a manner that is consistent (not in conflict) herewith.

Diaper 10 generally defines the longitudinally extending length direction 26; and the laterally extending width direction 24, as representatively shown in FIG. 1. The diaper may have any desired shape, such as rectangular, T-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and may have length and width dimensions which are generally larger than and extend beyond the corresponding dimensions of the absorbent structure 32 to provide for the corresponding side margins 20 and end margins 22. Optionally, the topsheet and backsheet layers may not be coextensive. The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. The intermediate, crotch region 16 lies between and interconnects the waistband regions 14 and 12, and comprises that portion of the diaper which, when worn, is positioned between the legs of the wearer and covers the lower torso of the wearer. Thus, the intermediate crotch region 16 is an area where repeated liquid surges typically occur in the diaper or other disposable absorbent article.

Backsheet 30 can typically be located along an outer-side surface of the absorbent body 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body. Backsheet 30 prevents the exudates contained in absorbent body 32 from wetting articles, such as bedsheets and overgarments, which contact diaper 10. In particular embodiments of the invention, backsheet 30 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or nonwoven fibrous web layer which has been totally or partially constructed or treated to impart the desired levels of liquid impermeability to selected regions that are adjacent or proximate the absorbent body. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type forms the outercover of a HUGGIES® ULTRATRIM diaper, which is commercially available from Kimberly-Clark Corporation. The backsheet 30 typically provides the outer cover of the article. Optionally, however, the article may include a separate outer cover component member which is additional to the backsheet.

Backsheet 30 may include a micro-porous, "breathable" material which permits gases, such as water vapor, to escape from the absorbent body 32 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minnesota. The backsheet may also be embossed or otherwise provided with a pattern or matte finish to exhibit a more aesthetically pleasing appearance.

In the various configurations of the invention, where a component, such as the backsheet 30 or the containment flaps 62 are configured to be permeable to gas while having a resistance and limited permeability to aqueous liquid, the liquid resistant component can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated Dec. 31, 1968.

Accordingly, the backsheet member 30 is sufficiently impermeable liquid and semi-liquid materials to substantially prevent the undesired leakage of waste materials, such as urine and feces. For example, the backsheet member can desirably support a hydrohead of at least about 45 centimeters (cm) substantially without leakage. The backsheet member 30 can alternatively support a hydrohead of at least about 55 cm, and optionally, can support a hydrohead of at least about 60 cm, or more, to provide improved benefits.

The size of the backsheet 30 is typically determined by the size of absorbent body 32 and the particular diaper design selected. Backsheet 30, for example, may have a generally T-shape, a generally T-shape or a modified hourglass shape, and may extend beyond the terminal edges of absorbent body 32 by a selected distance, such as a distance within the range of about 1.3 centimeters to 2.5 centimeters (about 0.5 to 1.0 inch), to provide at least a portion of the side and end margins.

The topsheet 28 presents a body-facing surface which is compliant, soft-feeling, and non-irritating to the wearer's skin. Further, the topsheet 28 can be less hydrophilic than absorbent body 32, and is sufficiently porous to be liquid permeable, permitting liquid to readily penetrate through its thickness to reach the absorbent body. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent body 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30.

Topsheet 28 and backsheet 30 can, for example, be joined to each other in at least a portion of the diaper periphery by attachment mechanisms (not shown) such as adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or an array of separate lines, swirls or spots of construction bonds may be used to affix the topsheet 28 to the backsheet 30. It should be readily appreciated that the above-described attachment mechanisms may also be employed to suitably interconnect, assemble and/or affix together the various other component parts of the articles which are described herein.

The absorbent body 32 provides an absorbent structure which can include a retention portion 48, such as the shown absorbent pad composed of selected hydrophilic fibers and high-absorbency particles, for holding and storing absorbed liquids and other waste materials. The absorbent body is positioned and sandwiched between the topsheet 28 and backsheet 30 to form the diaper 10. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure 32 can comprise a matrix of hydrophilic fibers, such as a web of cellulosic fluff, mixed with particles of high-absorbency material. In particular arrangements, absorbent body 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic; absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in absorbent body 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and alternatively is within the range of about 550–750 gsm to provide desired performance.

To improve the containment of the high-absorbency material, absorbent body structure 32 can include an overwrap, such as wrap sheet 74, which is placed immediately adjacent and around absorbent body 32 and may be bonded to the absorbent structure and to the various other components of the article. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 74, or at least the bodyside layer of the wrap sheet, may comprise a meltblown web composed of meltblown fibers, such as meltblown polypropylene fibers. Another example of absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of absorbent body 32. Such a configuration of the wrap sheet can, for example, facilitate the formation of a substantially complete sealing and closure around the peripheral edges of absorbent body 32. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 74 can extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearers skin, and the high porosity, lower basis weight outerside layer can help reduce costs.

Diaper 10 can also include a surge management layer 46 which helps to decelerate and diffuse surges of liquid that may be introduced into the absorbent body of the article. In the illustrated embodiment, for example, surge layer 46 can be located on an inwardly facing body side surface of topsheet layer 28. Alternatively, surge layer 46 may be located adjacent to an outer side surface of topsheet 28. Accordingly, the surge layer would then be interposed between topsheet 28 and absorbent body 32. Examples of suitable surge management layers 46 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 (attorney docket No. 11,256) which issued as U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 (attorney docket No. 11,387) which issued as U.S. Pat. No. 5,490,846; the entire disclosures of which are hereby incorporated by reference in a manner that is consistent herewith.

The wetness indicator provided by the present invention includes at least one appointed indicator section of said backsheet member 30 which includes a backsheet material having at least a polymer sheet layer 96. The indicator section of the backsheet member also includes a plurality of translucent windows 98 which are arranged in an area pattern and are formed by a selected thermal treatment of the polymer sheet layer. A selected, appointed layer of contrast material 44 is desirably attached to the article at an operative location which is interposed between an intended wearer of the article and the indicator section of the backsheet member. The contrast layer can have a first appearance through the translucent windows when said contrast material is dry, and has a visually different second appearance through the translucent windows when the contrast material is wetted with water.

The polymer sheet layer 96 may, for example, be provided by a composite polymer sheet layer which can include a core layer 92 laminated between two skin layers 90. The core layer can be composed of about 40% DOW NG3310, about 5.3% DOWLEX 4012, about 50% ECC FILMLINK 2029, and about 2000 ppm of B900. DOW NG 3310 (having a density of about 0.918 g/cc) is linear-low-density-polyethylene (LLDPE) obtained from Dow Chemical USA of Midland, Mich. The DOWLEX 4012 material (having a density of about 0.916 g/cc) is low-density-polyethylene (LDPE) from Dow Chemical USA of Midland, Mich. The FILMLINK 2029 material is calcium carbonate filler coated with behenic acid, obtained from English China Clay. CIBA B900 is an antioxidant package to provide thermal stability to the polymers during extrusion. The B900 material is a 1.4 ratio of IRGANOX 1076 (a phenolic anti-oxidant) and IRGAFOS 168 (a phosphite stabilizer), and is produced by Ciba Specialty Products. The skin layers 90 can be composed of about 45.1% MONTELL KS357, about 50.4% EXXON 768.36, about 4% SUPERFLOSS, and about 5000 ppm B900. The MONTELL KS357 material is a 30 meltflow rate, random copolymer, ethylene-propylene CATALLOY polymer; and the EXXON 768.36 material is an ethylene-vinyl acetate copolymer, which contains about 28 percent vinyl acetate. The SUPERFLOSS material is diatomaceous earth, produced by Celite Corp., a subsidiary of World Minerals of Lompoc, Calif. The composite polymer sheet 96 can be initially supplied at a basis weight within the range of about 85–98 g/m$^2$, and then operatively stretched about 4.7× to render it porous and breathable. The resulting polymer sheet layer 96 can then have a basis weight which is not less than about 12 g/m$^2$ and optionally is not less than about 26 g/m$^2$. In other aspects, the stretched sheet layer can have a basis weight which is not more than about 53 g/m$^2$, and optionally is not more than about 32 g/m$^2$ to provide desired benefits.

Figure 4:
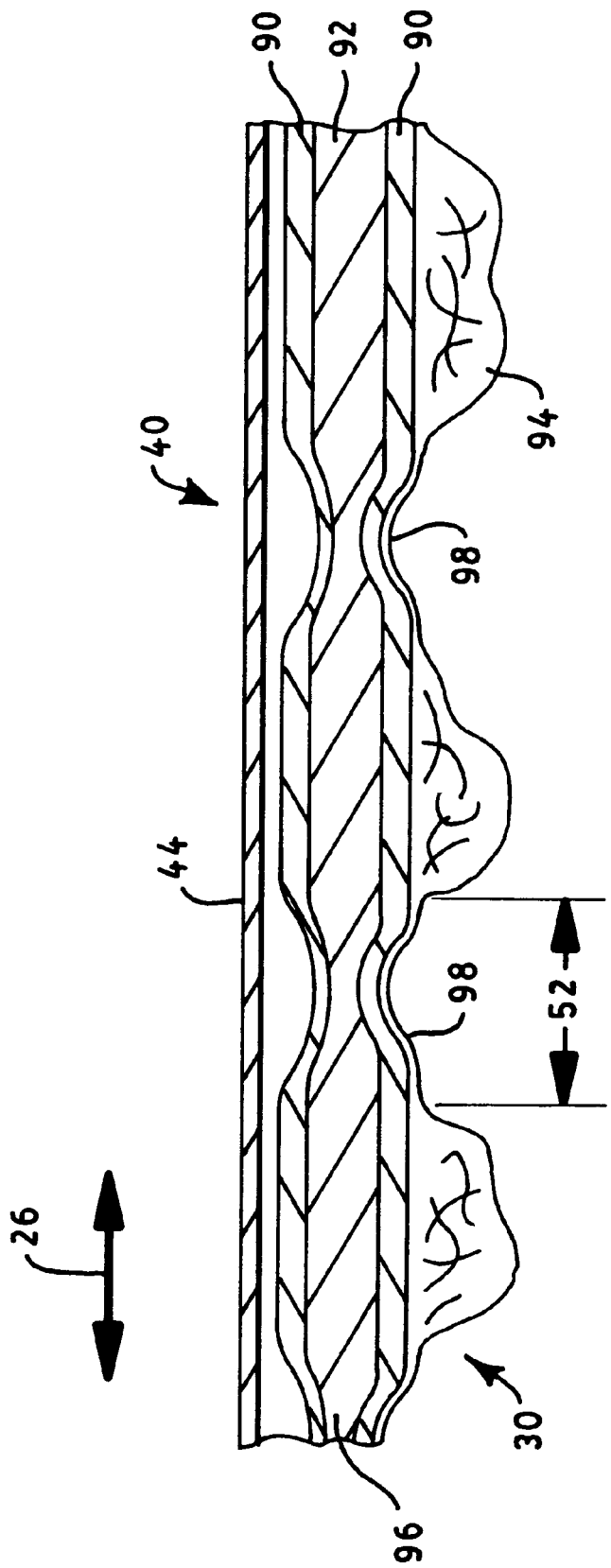
FIG. 4 shows an enlarged, cross-sectional view of the representative pattern of substantially translucent window areas formed across the surface area of the backsheet member.
Figure 7:
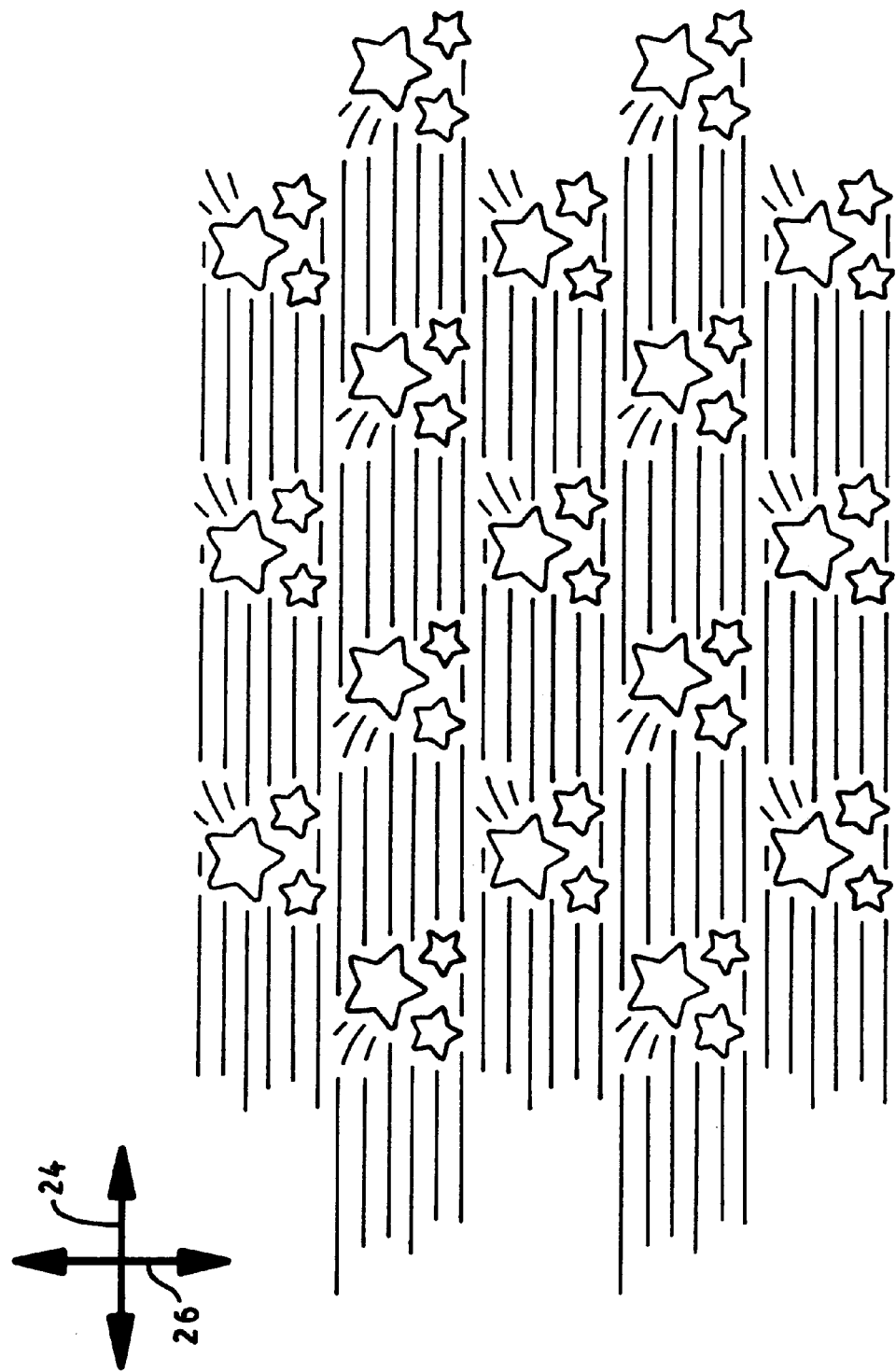
FIG. 7 shows an enlarged, top view of a representative pattern of the substantially translucent window areas formed across the outer surface area of the backsheet member.

With reference to FIGS. 4 and 7, a further aspect of the invention can include a wetness indicator system wherein at least the appointed indicator section of the backsheet 30 includes a laminate material having at least one fibrous nonwoven web 94 which is attached to the polymer sheet layer 96. The nonwoven fabric 94 may, for example, be a spunbonded nonwoven, such as a polypropylene spunbond, nonwoven fabric. Additionally, the fabric can have a basis weight which is not less than a minimum of about 6.8 g/m$^2$ (about 0.2 oz/yd$^2$). Alternatively, the basis weight is not less than about 10.2 g/m$^2$ (about 0.3 oz/yd$^2$) and optionally, is not less than about 13.6 g/m$^2$ (about 0.4 oz/yd$^2$). In other aspects, the fabric can have a basis weight of not more than a maximum of about 55 g/m$^2$. Alternatively, the basis weight can be not more than about 51 g/m$^2$ (about 1.5 oz/yd$^2$), and optionally, can be not more than about 41 g/m$^2$ (about 1.2 oz/yd$^2$). In still other aspects, the basis weight can be not more than about 27.2 g/m$^2$ (about 0.8 oz/yd$^2$).

Examples of suitable nonwoven fibrous webs can include webs composed of polypropylene, polyester, nylon, polyethylene as well as combinations thereof. The fibers may have a bicomponent or other multi-component configuration, and the webs may be spunbond fabrics, bonded-carded webs or meltblown fabrics, as well as combinations thereof.

With reference to FIGS. 5 and 6, particular aspects of the invention can have the polymer sheet layer 96 configured as a composite sheet having a core layer 92 sandwiched between a pair of skin layers 90 to provide an A-B-A type of film construction. Desirably, the sheet layer is sufficiently gas permeable to be breathable. Suitable techniques and materials for constructing an appropriate polymer sheet layer 96 are described in U.S. patent application Ser. No. 08/882,712 of A. McCormack et al., entitled LOW GAUGE FILMS AND FILM/NONWOVEN LAMINATES and filed Jun. 25, 1997 (attorney docket No. 11,436.2), the entire disclosure of which is incorporated herein by reference in a manner that is consistent herewith. Other materials which may be suitable are described in PCT application WO 95/16562 of A. McCormack, filed Jun. 22, 1995 and entitled BREATHABLE CLOTH-LIKE FILM/NONWOVEN COMPOSITE; the entire disclosure of which is incorporated herein by reference in a manner that is consistent herewith.

In another aspect of the invention, the sheet layer 96 can include a linear-low-density-polyethylene (LLDPE) which is desirably present in at least the core layer 92. At least one and desirably both of the skin layers 94 have a composition which is readily compatible with both the nonwoven fabric web 94 and the core layer 92. In particular, the skin layers are configured to readily attach to the nonwoven web 94 upon the application of bonding techniques employing heat and/or pressure. Such techniques can, for example, include thermal bonding, sonic bonding and the like, as well as combinations thereof. Accordingly, the configuration can achieve a sufficiently strong, fused bond between the breathable, stretch-opacified, prominently LLDPE polymer sheet layer 96 and the nonwoven fabric layer 94. The resulting backsheet member 30 can thereby achieve a sufficient level of durability and abrasion resistance desired for an outer cover component.

In a further aspect of the invention, the selected polymer sheet layer 96, particularly the sheet layer composed of the A-B-A LLDPE film, is stretched in a particular manner after it is extruded, formed and cooled. The post-extrusion stretching can produce microscopic holes between the primary polymer material and the calcium carbonate particles contained and distributed within the polymer material, thereby providing the breathability function in the composite backsheet member 30. Additionally, the stretching can produce a stretch-opacifying (e.g. "stretch-whitening") of the sheet layer 96. This stretching can render the film opaque or white because of various mechanisms. For example, as the film is stretched, the primary polymer material pulls away from the calcium carbonate particles, thereby producing micropores that refract and scatter incident light. Additionally, the stretching process strains the polymer material past its yield point, thereby imparting a molecular orientation to the primary polymer material. The resulting opacity or whiteness is sufficient to block an observer's view of the wetness that becomes present within the article.

The subsequent gross pattern embossing and fusing operation can employ a concentration of heat and pressure at sufficient amounts which operatively meld the nonwoven fabric web 94 with the polymer sheet layer 96. The melding affixes the fabric web to the polymer sheet with a strength sufficient to provide suitable durability in the backsheet member. Within the sheet layer 96, the skin layer 90 by virtue of its polymer composition, has a melting point which is intermediate that of the polypropylene fibers and the core layer 92. This causes the skin layer to act as a "meltable intermediary" between the fabric web 94 and the core layer 92. In those areas where the opaque sheet layer 96 becomes melted and reflowed, the sheet layer can regain an amorphous molecular orientation and can regain a desired level of translucency. Thus, the gross pattern embossment operation can substantially simultaneously affix together the fabric web 94 and the polymer sheet 96 while also rendering the resulting composite translucent within the area of the fused bonds.

In a representative configuration, the backsheet member 30 can, for example, include a fibrous nonwoven web 94 composed of spunbonded polypropylene fibers, and having a fabric basis weight within the range of about 14–17 g/m$^2$. The nonwoven fibrous web 94 includes about 2 percent titanium dioxide pigment, and is consolidated with a wire weave point bonding pattern. The fiber size is about 2 denier per filament (dpf), but could include fiber sizes within the range of about 1–2.5 dpf.

In the representative example of the material for the backsheet member, the cooperating polymer sheet layer 96 can include a core layer 92 composed of about 40%, DOW NG3310, about 5.3% DOWLEX 4012, about 50% ECC FILMLINK 2029, and about 2000 ppm of B900. DOW NG 3310 (having a density of about 0.918 g/cc) is linear-low-density-polyethylene (LLDPE) obtained from Dow Chemical USA of Midland, Mich. The DOWLEX 4012 material (having a density of about 0.916 g/cc) is low-density-polyethylene (LDPE) from Dow Chemical USA of Midland, Mich. The FILMLINK 2029 material is calcium carbonate filler coated with behenic acid, obtained from English China Clay. CIBA B900 is an antioxidant package to provide thermal stability to the polymers during extrusion. The B900 material is a 1:4 ratio of IRGANOX 1076 (a phenolic anti-oxidant) and IRGAFOS 168 (a phosphite stabilizer), and is produced by Ciba Specialty Products. Laminated to each side of the core layer 92 are skin layers 90 which are composed of about 45.1% MONTELL KS357, about 50.4% EXXON 768.36, about 4% SUPERFLOSS, and about 5000 ppm B900. The MONTELL KS357 material is a 30 meltflow rate, random copolymer, ethylene-propylene CATALLOY polymer; and the EXXON 768.36 material is an ethylene-vinyl acetate copolymer, which contains about 28 percent vinyl acetate. The SUPERFLOSS material is diatomaceous earth, produced by Celite Corp, a subsidiary of World Minerals of Lompoc, Calif. The composite sheet 96 can be initially supplied at a basis weight within the range of about 57–65 g/m$^2$, and then operatively stretched about 4.7× to render it breathable. The resulting polymer sheet layer 96 can then have a basis weight which is not less than about 8 g/m$^2$, and optionally is not less than about 17 g/m$^2$. In other aspects, the stretched sheet layer can have a basis weight which is not more than about 35 g/m$^2$, and optionally is not more than about 21 g/m$^2$ to provide desired benefits.

The LLDPE sheet layer 96 can lend itself to producing the translucent gross pattern embossments for various reasons. For example, this polymer needs only 50 percent calcium carbonate loading (as opposed a 60 percent for polypropylene polymer) to provide the same target WVTR performance. In addition, the LLDPE polymer has a more amorphous molecular orientation, as compared to polypropylene. The lower calcium carbonate loading and the more amorphous structure can help make the LLDPE sheet layer 96 less liable to split. The lower calcium carbonate loading in LLDPE help makes it more translucent, and the LLDPE sheet layer can be run at lower basis weight. Also, the LLDPE has a lower melting point. As a result, less energy is required in the individual gross pattern embossments to achieve sufficient film and nonwoven melting to produce the desired levels of translucency in the appointed window areas 98. Thus, the LLDPE sheet layer 96 can better achieve desired levels of aesthetics, durability, translucency and manufacturing speed.

In the various configurations of the invention, the nonwoven web 94 and the polymer sheet layer 96 can be thermally bonded together to form the bonding array of gross pattern embossments which are shared between the polymer sheet layer 96 and the nonwoven web 94. The amount of bonding area provided by the shared gross pattern embossment, the basis weight and inherent shred-resistance of the nonwoven web 94, the relatively low extensibility under tension of the nonwoven web, and the inherent strength and stretch properties of the polymer sheet layer 96 (particularly the sheet layer having LLDPE) can all contribute to the desired operability of the present invention. Additionally, the selected configurations of nonwoven web 94 and the material in the core layer 92 of the polymer sheet 96 (such as the core layer configuration containing LLDPE material) can advantageously cooperate to generate translucent gross embossment sites in at least the appointed indicator section of the backsheet member 30. The resulting laminate can serve as the breathable, moisture impermeable outer cover for a disposable absorbent product, such as a diaper. The inside surface of the outer cover laminate, which is typically provided by the inward facing surface of the sheet layer 96, can operatively receive the application of bonding materials, such as swirl sprays or other patterns of hot melt construction adhesive, to provide the attachments which join the absorbent body 32 to the inward surface of the backsheet member 30, and which join the topsheet 28 to the backsheet member at the perimeter around the absorbent body 32.

The gross pattern embossing, and heat/pressure fusing operation can advantageously provide a combination of different functions. The gross pattern fusing operation attaches and affixes together the nonwoven web 94 and the polymer sheet layer 96 to assemble and laminate the backsheet member 30. The gross pattern embossments also provide the overall decorative pattern and a desirable three-dimensionality to the outward surface of the backsheet member outer cover laminate which connotes durable, apparel-like fabric having desired visual and tactile qualities. In addition, the fusing operation can produce a substantially corresponding pattern of translucent window areas 98 which can operatively transmit the change in appearance (e.g. change in color) of the associated contrast layer material 44 (e.g. pigmented tissue layer) when the contrast layer 44 becomes wet.

Another aspect of the invention can include a composite backsheet member 30 which is formed by adhesively laminating the nonwoven web 94 to the polymer sheet layer 96. A subsequent thermal processing operation which applies heat and pressure can then be employed to form gross, pattern embossments and a pattern array of window areas 98 in the indicator section of the backsheet member.

In further aspects of the invention, the resulting composite backsheet member 30 is sufficiently gas-permeable to be deemed breathable. In desired configurations, the backsheet member can provide a WVTR value which is not less than a minimum of about 500 grams per square meter per 24 hours. The WVTR value can be not less than about 1000 grams per square meter per 24 hours, and optionally, can be not less than about 1500 grams per square meter per 24 hours to provide improved humidity control and performance. In further configurations, the backsheet member 30 can have a WVTR of up to about 5000 grams per square meter per 24 hours, or more, to provide further benefits. The WVTR value of a material can be determined in accordance with ASTM Standard E96-80.

Other aspects of the backsheet member 30 can further have an interlaminar peel strength which is at least about 22.5 grams-force per inch of width, and optionally, is at least about 45 grams-force per inch. In other aspects, the backsheet member can have a peel strength which is up to about 75 grams-force per inch, and optionally, is up to the maximum force that can be sustained by the component layers of the backsheet member during a peeling operation. For example, the desired peel strength can be provided between the outward nonwoven web 94 and the polymer sheet 96 of the backsheet member 30.

To determine the interlaminar peel strength, a laminate is tested for the amount of tensile force which will pull apart the layers of the laminate. Values for peel strength are obtained using a specified width of fabric, clamp jaw width and a constant rate of extension. For samples having a film side, the film side of the specimen is covered with masking tape, or some other suitable material, in order to prevent the film from ripping apart during the test. The masking tape is on only one side of the laminate and so does not contribute to the peel strength of the sample. This test uses two clamps, each clamp having two jaws with each jaw having a facing in contact with the sample, to hold the material in the same plane, usually vertically, separated by 2 inches to start. The sample size is 4 inches (10.2 cm) wide by as much length as is necessary to delaminate a sufficient amount of sample length. The jaw facing size is 1 inch (2.54 cm) high by at least 4 inches (10.2 cm) wide, and the constant rate of extension is 300 mm/min. The sample is delaminated by hand in an amount sufficient to allow it to be clamped into position. During testing, the clamps move apart at the specified rate of extension to pull apart the laminate. The sample specimen is pulled apart at 180° angle of separation between the two layers, and the peel strength reported is an average of three tests, each of which gather data regarding peak load in grams. The measurement of the desired peeling force data begins when a 16 mm length of the specimen laminate has been pulled apart and delaminated, and the measurement continues until a total of 170 mm of the specimen length has been delaminated. A suitable device for determining the peel strength testing is a SINTECH 2 tester, available from the Sintech Corporation, a business having offices at 1001 Sheldon Dr., Cary, N.C. 27513; or an INSTRON Model TM, available from the Instron Corporation, a business having offices at 2500 Washington St., Canton, Mass. 02021; or the Thwing-Albert Model INTELLECT II available from the Thwing-Albert Instrument Co., a business having offices at 10960 Dutton Rd., Philadelphia, Pa. 19154. The test may be performed in the cross-direction (CD) 24 of the selected specimen or in the longitudinal direction 26 of the selected specimen from the article.

In further aspects, the backsheet member can exhibit a peak strain value along the longitudinal direction 26 which is at least about 20%, and optionally is at least about 30%. In other aspects, the backsheet member can exhibit a peak strain value along the longitudinal direction 26 which is up to about 40%. Alternatively, the peak strain value can be up to about 60%, and optionally can be up to about 100%, or more, to provide improved performance. The peak strain value can be determined in accordance with standard procedure ASTM D1117-80 and ASTM D5035-90.

Additional aspects of the backsheet member can provide a Taber abrasion value which is at least about 150 cycles, and optionally, is up to about 200 cycles, or more, to provide improved performance. The Taber abrasion value can be determined in accordance with standard procedure FTM-191A, Method 5306. The abrasion measurements are made using a TABER Standard Abrader (Model 503) with rubber wheels #S-32 and a 125 gram counterweight (total load of 125 gram).

In the appointed indicator section of the backsheet member 30, the pattern bonding and embossing of the backsheet member can be configured to also produce a plurality of translucent windows 98 which are arranged in an area pattern and are desirably formed by the selected thermal bonding of the fibrous nonwoven web 94 to the polymer sheet layer 96 within the backsheet laminate. The nonwoven web 94 and polymer sheet layer 96 are selectively configured to interact upon the application of heat or upon the application of heat and pressure to cooperatively form the operative translucent window areas 98.

With reference to FIG. 7 pattern array of window areas 98 can be configured in a C-Star pattern composed of a plurality of window lines arranged in the shape of different size stars, and plurality of window lines arranged as laterally extending stripes.

Each translucent window 98 has a substantially contiguous translucent area of at least of a minimum of about 0.4 mm$^2$. The contiguous area of the translucent window is alternatively at least about 0.6 mm$^2$, and optionally is at least about 1 mm$^2$ to provide desired benefits. In other aspects, the area of each window can be up to about 38 mm$^2$, and optionally, can be up to about 130 mm$^2$ to provide improved performance.

In additional aspects, each translucent window has a relatively smaller dimension, window height 52 which is at least a minimum of about 0.01 inches (about 0.254 mm). The window height is alternatively at least about 0.02 inches (about 0.51 mm), and optionally, is at least about 0.05 inches (about 1.27 mm) to provide improved performance. In addition, each translucent window area can have a relatively larger dimension, window length 54 which is at least about 0.0625 inches (about 1.59 mm), and desirably can be at least about 0.125 inch (about 3.2 mm). Alternatively, the window length can be at least about 1 inch (about 25.4 mm), and optionally, can be at least about 3 inches (about 76.2 mm), or more, to provide further improved benefits.

In the illustrated configuration, each translucent window is desirably formed by a thermal bonding of the polymer layer 96 to the nonwoven layer 94 within the composite structure of the backsheet member 30. The thermal bonding, or other operative thermal treatment, provides sufficient heat and or pressure energy to melt and re-flow the materials of the backsheet member, particularly the nonwoven fabric 94 and the polymer sheet layer 96, to render the resultant, bonded composite sufficiently translucent within the areas of the thermal bonds.

The bonding of the polymer layer 96 to the nonwoven fabric layer 94 within the composite laminate material of the indicator section of the backsheet member 30 can provide a total thermal bonding area which is at least about 11% of an overall area of the backsheet member 30. The total bonding area can alternatively be at least about 14%, and optionally, is at least about 18% of the overall area of the backsheet member. In other aspects, the thermal bonding area can be up to about 25%, and alternatively can be up to about 45%, or more to provide desired benefits.

In further aspects of the invention, the bonding of the polymer layer 96 to the nonwoven fabric layer 94 within the backsheet member 30 within the indicator section of the backsheet member provides a total translucent window area which is at least about 11% of the overall area of the appointed indicator section of the backsheet member. The total translucent window area is alternatively at least about 14%, and optionally, is at least about 18% of the overall area of the appointed indicator section of the backsheet member. In other aspects, the translucent window area can be up to about 25%, and alternatively can be up to about 45%, or more to provide desired benefits. In desired aspects, such percentage area of the window areas 98 is provided over at least about 1 inch$^2$ (about 6.4 cm$^2$) of the appointed indicator section of the backsheet member 30. Alternatively, such percentage area of the window areas is provided over at least about 12.8 cm$^2$, and optionally, is provided over at least about 25.6 cm$^2$ of the appointed indicator section. In other aspects, the translucent window area 98 are located in an indicator section which is superposed with the absorbent body structure 32 of the article. Desirably, the translucent window area shall encompass an indicator section area which is superposed with the front 80% of the absorbent structure. More desirably, the translucent window areas 98 are in an indicator section area which is superposed with the front 60% of the absorbent structure.

The selectively employed contrast layer 44 may be provided by a separately provided, additional layer of material assembled into the article, and may be provided by various suitable materials. For example, the contrast layer may be provided by a tissue layer, a nonwoven fabric layer, a film material, a net material, a scrim material or the like, as well as combinations thereof. In addition, the contrast layer may be treated or otherwise modified to produce the desired contrast between the first appearance when the contrast layer is dry and the second appearance when the contrast layer is wet.

Alternatively, the contrast layer 44 may be integrally provided by a component that is already present in the article. For example, the layer of contrast layer material may be integrally provided by the material employed to form the absorbent wrap 74, or the material employed to form the absorbent body 32.

In particular aspects of the invention, the contrast layer 44 has a relatively lighter appearance when dry, and a relatively darker appearance when wetted with water. Optionally, the contrast layer 44 can have a relatively darker appearance when dry, and a relatively lighter appearance when wetted with water, as desired.

In particular configurations, the contrast layer 44 can have a first color when the contrast layer is dry, and a visually different, second color when the contrast layer is wetted with water. For example, the contrast layer 44 may be provided by a layer of colored tissue which has a first color when it is dry and a visually darker color when the tissue is wetted with water.

At least a portion of the contrast layer 44 is optically aligned with the translucent window areas 98. As a result, the translucent window areas 98 which are positioned substantially adjacently over a wetted section of the contrast layer 44 will have a visually different appearance, as compared to the appearance observed through the translucent windows 98 which are positioned over the unwetted sections of the contrast layer 44.

The contrast layer 44 can be positioned in any operative positions which is interposed between an intended wearer of the article and the indicator section of the backsheet member 30. For example, the contrast layer 44 can be located adjacent to the absorbent body 32. In particular, the contrast layer can be located between the absorbent body 32 and the backsheet member 30. Alternatively, the contrast layer 44 can be positioned between the absorbent body 32 and the topsheet layer 28. The contrast layer 44 can advantageously cooperate with the indicator section of the backsheet 30 to provide a first appearance when dry, and a visually different second appearance when wetted with water.

When the selected configuration of the product of the invention is in its dry condition, the desired backsheet member 30 material does not exhibit a sufficient color contrast between the translucent window areas 98 and the relatively non-translucent portions of the backsheet member 30. This can be particularly apparent in the indicator section of the backsheet member. When the product is in a wet condition, the indicator section of the backsheet member 30 material can exhibit an operative, visually distinct color or shading contrast between the translucent windows 98 and the relatively less translucent portions of the backsheet member 30 which are immediately adjacent to the translucent window areas. The operating areas of the indicator section can have a distinctive first appearance when appointed, correspondingly adjacent portions of the article at the translucent windows are dry, and can have a distinctive, visually different second appearance when appointed, adjacent portions of the article at the translucent windows are wetted with water. For example, the operative contrast or relative ratio of light transmission and/or reflective properties at the translucent window areas can desirably cooperate with the appointed contrast layer 44 to provide the wetness indicator of the invention.

A product incorporating the desired indicator section can, for example, be assessed with the following three tests:
  Hunter (L*a*b*);
  Tristimulus (X,Y,Z); and
  Chromaticity (x) combined with Whiteness Index (WI).
  Product samples are tested in both the wet and dry states, and the wet product samples are prepared by adding an operative amount of a saline that is representative of human urine.

In the various aspects of the invention, the visual difference which can be observed between the first appearance of the dry indicator section of the backsheet member 30 and the second appearance of the wet indicator section of the backsheet member can be defined by a wet-dry Contrast Ratio value, as determined with Hunter (L*a*b*) color coordinates, which is at least a minimum of about 1.2. Alternatively, the Contrast Ratio value can be at least about 1.5, and optionally can be at least about 2 to provided improved performance. Desirably, the Contrast Ratio value can be at least about 2.5, and can be at least about 3, or more, to provide further improved benefits and distinctiveness. For example, the Hunter Contrast Ratio value can be up to about 10. The Contrast Ratio value can alternatively be up to about 20, and can optionally be up to about 30 or more, as desired.

The visual difference between the first appearance of the dry indicator section of the backsheet member 30 and the second appearance of the wet indicator section of the backsheet member can also be defined by a wet-dry Contrast Ratio value, as determined with Tristimulus (X,Y,Z) color coordinates, which is at least a minimum of about 1.1. Alternatively, the Contrast Ratio value can be at least about 1.2, and optionally can be at least about 2 to provided improved performance. Desirably, the Contrast Ratio can be at least about 2.5, and can be at least about 3, or more, to provide further improved benefits and performance. For example, the Tristimulus Contrast Ratio value can be up to about 10. The Contrast Ratio value can alternatively be up to about 20, and can optionally be up to about 30 or more, as desired.

The visual difference between the first appearance of the dry indicator section of the backsheet member 30 and the second appearance of the wet indicator section of the backsheet member can further be defined by a wet-dry Contrast Ratio value, as determined with Chromaticity (x) combined with Whiteness Index (WI), which is at least a minimum of about 1.1. Alternatively, the Contrast Ratio value can be at least about 1.2, and optionally can be at least about 2 to provided improved performance. Desirably, the Contrast Ratio can be at least about 2.5, and can be at least about 3 to provide further improved benefits and distinctiveness. For example, the Chromaticity Contrast Ratio value can be up to about 10. The Contrast Ratio value can alternatively be up to about 20, and can optionally be up to about 30 or more, as desired.

Suitable techniques for determining the Contrast Ratio values can be provided by the procedures set forth below in the "Testing—Appearance" section of the present description.

In desired configurations, at least a portion of the indicator section of the backsheet member 30 is positioned in the intermediate, crotch section 16 of the article. In desired arrangements, the indicator section can have an indicator length which extends longitudinally from the crotch section of the diaper up to a line which is not less than about 3 cm from the longitudinally terminal edge of the front waistband portion 14. In addition, the length of the indicator section can extend longitudinally from the crotch section of the diaper up to a line which is located not less than about 3 cm away from the longitudinally terminal edge of the rear waistband portion 12. Further aspects of the invention can include an indicator section which extends up to a line which is positioned not less than about 10 cm away from the longitudinally terminal edge of either or both of the front and rear waistband portions. Optionally, the indicator section can extend over substantially the entire area of the backsheet member 30.

Desired configurations can have the layer of contrast material 44 interposed between the indicator section of the backsheet member 30 and the retention portion 48. Optional arrangements can have the layer of contrast material interposed between the topsheet layer 28 and the retention portion 48.

The leg elastic members 34 are located in the lateral side margins 20 of diaper 10, and are arranged to draw and hold diaper 10 against the legs of the wearer. The elastic members are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other mechanisms, such as heat-shrink elastic material, may be used to gather the garment.

In the embodiment illustrated in FIG. 1, the leg elastic members 34 extend essentially along the complete length of the intermediate crotch region 16 of diaper 10. Alternatively, elastic members 34 may extend the entire length of diaper 10, or any other length suitable providing the arrangement of elastically contractible lines desired for the particular diaper design.

The elastic members 34 may have any of a multitude of configurations. For example, the width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of Lycra elastomer available from DuPont, a business having offices in Wilmington, Delaware. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 10 can include a waist elastic 42 positioned in the longitudinal margins of either or both of the front waistband 14 and the rear waistband 12.

The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge 76 to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (FIG. 1).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along an ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24. For example, suitable meltblown elastomeric fibrous webs for forming ear regions 38 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30, and a second pair of ear regions extend laterally at the opposed lateral ends of the front waistband section of the backsheet. The illustrated ear regions have a tapered, curved or otherwise contoured shape in which the length of the base region is smaller than the length of its relatively outboard end region. Alternatively, the ear regions may have a substantially rectangular shape or a substantially trapezoidal shape.

Diaper 10 can also include a pair of elasticized containment flaps 62 which extend generally length-wise along the longitudinal direction 26 of the diaper. The containment flaps are typically positioned laterally inboard from leg elastics 34, and substantially symmetrically placed on each side of the lengthwise, longitudinal centerline of the diaper. In the illustrated arrangements, each containment flap 62 has a substantially fixed edge portion 64 and a substantially moveable edge portion 66, and is operably elasticized with at least one elastomeric member 68 to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT (attorney docket No. 11,375), which corresponds to U.S. Pat. No. 5,562,650, the disclosure of which is hereby incorporated by reference in a manner that is consistent herewith.

In optional, alternative configurations of the invention, diaper 10 may include internal, elasticized, containment waist flaps, such as those described in U.S. Pat. No. 4,753,646 issued Jun. 28, 1988, to K. Enloe, and in U.S. patent application Ser. No. 560,525 of D. Laux et al. entitled AN ABSORBENT ARTICLE WITH IMPROVED ELASTIC MARGINS AND CONTAINMENT SYSTEM and filed Dec. 18, 1995 (attorney docket No. 11091), the entire disclosures of which are hereby incorporated by reference in a manner that is consistent herewith. Similar to the construction of the containment flaps, the containment waist flaps may be composed of a wettable or non-wettable material, as desired. The waist flap material may be substantially liquid-impermeable, permeable to only gas, or permeable to both gas and liquid.

To provide a desired refastenable fastening system, diaper 10 can include one or more appointed landing member regions, such as a first, primary landing member 50 (e.g. FIG. 2), which can provide an operable target area for receiving a releasable and re-attachable securement of the fastener tabs 36 thereon. In particular embodiments of the invention, the landing member patch can be positioned on the front waistband portion 14 of the diaper and is located on the outward surface of the backsheet layer 30. Alternatively, the landing member patch can be positioned on an appointed inward surface of the diaper, such as the bodyside surface of the topsheet layer 28. The fastening mechanism between the landing member and the fastener tabs 36 may be adhesive, cohesive, mechanical or combinations thereof. In the context of the present invention, a mechanical fastening system is a system which includes cooperating components which mechanically inter-engage to provide a desired securement.

A configuration which employs a releasable, interengaging mechanical fastening system can, for example, locate a first element of the mechanical fastener on the landing member 50 and a second, cooperating element of the mechanical fastener on the fastener tab 36. For example, with a hook-and-loop fastener, the hook material can be operably connected and affixed to the fastener tabs 36 and the loop material can be operably connected and affixed to the landing member 50. Alternatively, the loop material can be operably connected to the fastener tabs 36 and the hook material can be operably connected to the landing member.

In the various embodiments of the invention, a separately provided tape fastener tab 36 can be located at either or both of lateral end regions 86 and 88 of either or both of the waistbands 14 and 12. The representatively shown embodiment, for example, has one of the fastener tabs 36 located at each of the distal side edges of the rear waistband 12. More particularly, each of the fasteners 36 is assembled and attached to extend from a corresponding, immediately adjacent ear region at one of the opposed lateral ends of the back waistband section 12.

In the various configurations of the invention, the first and/or second fastening component may include an adhesive, a cohesive, a complementary element of an interengaging mechanical fastening system, or the like, as well as combinations thereof. The mechanical fastener components can be provided by mechanical-type fasteners such as hooks, buckles, snaps, buttons and the like, which include cooperating and complementary, mechanically interlocking components. For example, the mechanical fastening system may be a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single or multiple hook configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

In desired arrangements of the invention, the first fastening component 52 and/or the second fastening component 100 may include a hook type of mechanical fastening element. Accordingly, the corresponding first landing member component 52 and/or second landing member component 102 can include a complementary loop element. It should also be readily apparent that, in the various configurations of the invention, the relative positions and/or materials of the fastening component and its corresponding landing member component can be transposed. For example, in a hook-and-loop fastening system, the first and/or second fastening component may optionally be composed of a loop element and the first and/or second landing member components may be provided by a hook-type element.

Examples of suitable hook-and-loop fastening systems are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. (attorney docket No. 11,571) which corresponds to U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et all., entitled MECHANICAL FASTENING SYSTEM WITH GRIP TAB and filed Mar. 6, 1996 (attorney docket No. 12,563) which corresponds to U.S. Pat. No. 5,624,429 issued Apr. 29, 1997, the entire disclosure of which is hereby incorporated by reference in a manner which is consistent herewith.

In a typical configuration of a hook-and-loop fastening system, the hook material member is operably connected to the fastening tab 36, and the loop material is employed to construct at least one cooperating landing member 50. The landing member can, for example, be suitably positioned on the exposed, outward-side surface of the backsheet 30. As previously mentioned, an alternative configuration of the hook-and-loop fastening system may have the loop material secured to the fastener tab 36 and may have the hook material employed to form the landing member 50.

In the various aspects and configurations of the invention, the hook element material can be of the type referred to as micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.033–0.097 cm (about 0.013 to 0.038 inch); and a cap width which is within the range of about 0.025–0.033 cm (about 0.01 to 0.013 inch). The hooks are attached to a base film substrate having a thickness of about 0.0076–0.01 cm (about 0.003–0.004 inch) and a Gurley stiffness of about 15 mgf.

Another suitable micro-hook material is distributed under the designation VELCRO CFM-29 1058, and is available from VELCRO U.S.A., Inc., a business having offices in Manchester, N.H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch), and the member of hook material has a Gurley stiffness of about 12 mgf (about 12 Gurley units).

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensborough, N.C. under the trade designation #34285, as well other of knit fabrics. Suitable loop materials are also available from the 3M Company, which has distributed a nylon woven loop under their SCOTCHMATE brand. The 3M Company has also distributed a linerless loop web with adhesive on the backside of the web, and 3M knitted loop tape.

In particular aspects of the invention, the loop material need not be limited to a discrete landing member patch. Instead the loop material can, for example, be provided by a substantially continuous, outer fibrous layer which is integrated to extend over substantially the total exposed surface area of a cloth-like outer cover employed with the diaper 10. The resultant, cloth-like backsheet 30 can thereby provide the loop material for an operative "fasten anywhere" mechanical fastening system.

In the various configurations of the invention, the engagement force between the particular fastening component and its appointed landing member component should be large enough and durable enough to provide an adequate securement of the article on the wearer during use. In desired configurations, the engagement force can provide a peel force value of not less than about 75 grams-force (gmf). Alternatively, the peel force is not less than about 100 gmf, and optionally is not less than about 400 gmf. In particular aspects, the peel force is not more than about 1,200 gmf. Alternatively, the peel force is not more than about 800 gmf, and optionally is not more than about 600 gmf. The engagement force can additionally provide a shear force value of not less than about 1,000 gmf. Alternatively, the shear force is not less than about 2,000 gmf, and optionally, is not less than about 3,000 gmf. In further aspects, the shear force is not more than about 10,000 gmf. Alternatively, the shear force is not more than about 9,000 gmf, and optionally is not more than about 8,000 gmf.

The peel force can be determined in accordance with standard procedure ASTM D5170, approved Sep. 15, 1991 and published November 1991. The shear force value can be determined in accordance with the standard procedure ASTM D-5169, approved Sep. 15, 1991 and published November 1991.

Each of the fastening components and elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with the associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing member of the article.

Testing—Appearance

Product incorporating the desired indicator section (e.g.; backsheet member 30 in conjunction with a layer of contrast material 44, such as colored tissue) can be assessed with the following three tests:

Hunter (L*a*b*);
Tristimulus (X,Y,Z); and
Chromaticity (x) combined with Whiteness Index (WI).

Product samples are tested in both the wet and dry states. For the various wet samples, 160 ml of saline solution obtained from Ricca Chemical Company, Arlington, Tex. as Sodium Chloride, 0.9 percent weight-to-volume Aqueous solution of Isotonic Saline were added to the area being measured. The saline solution was gently poured onto the sample at a single location, using a standard 250 ml beaker for wetting, allowing the liquid to permeate the diaper absorbent material. The entire diaper was taken and measured near the area where the saline was introduced by placing the whole diaper outer cover against the exit slit of the spectrophotometer integrating sphere. Measurements were taken after approximately 2–5 minutes following the saline addition. The masking slit was placed over the diaper outer cover to define the sampling area as either bonded or non-bonded.

Spectrum Acquisition

Transmission measurements were made using a Varian Cary 5G REF UV-Vis-NIR spectrophotometer instrument obtained from Varian Analytical Instruments, a business having offices at 505 Julie Rivers Road, Sugar Land, Tex. 77478, USA. The instrument was configured with a 150 mm inner diameter, integrating sphere coated with SPECTRALON diffuse reflectance standard material. The SPECTRALON material is available from Labsphere, a business having offices at Shaker Street, North Sutton, N.H. 03260, USA. The spectrophotometer instrument has a wavelength range of 175–3300 nm (nanometer) with nitrogen purge, and a photometric range of 7.0 A (Absorbance units). The instrument is certified to meet or exceed all of the following specifications: Stray Light: less than 0.00008% T at 220 nm, less than 0.00008% T at 370 nm, and less than 0.00045% T at 1420 nm using ASTM Methodology. Wavelength accuracy is ±0.1 nm (plus or minus 0.1 nm), with reproducibility of less than 0.025 nm using peak separation method; and exhibits less than 0.008 nm standard deviation of 10 measurements within the 300–700 nm range. The photometric accuracy for the system using NIST 930D Filters is ±0.003 A at 1.0 A and ±0.002 at 0.5 A. Photometric noise is less than 0.00005 A RMS at 0.0 A, and is less than 0.00015 A RMS at 1.0 A. Baseline flatness is ±0.001 A for the entire measurement region.

The measurement conditions for the bulk transmission measurements included: 400 to 700 nm scan range; slit band width (SBW) of 2.0 nm; scan rate of 300 nm/min.; 1.0 nm data interval; Energy (gain) at 1.0; response time setting at 0.2; baseline correction using SPECTRALON standard material; with integrating sphere bulk transmission measurement geometry. Bond site and non-bonded site measurements were made by masking the sample channel aperture at the sphere sample entrance port; background correcting without the presence of a sample, and making measurements by aligning the measurement area of the sample with the masking slit having internal aperture dimensions of 1.5 mm×25 mm (width×height).

Reflectance measurements were made with the instrument and sample slit settings identical to those for the transmission measurements, excepting that the sample and slit holder were positioned at the sphere sample exit port having a 25 mm inner diameter. Reference measurements were made with the SPECTRALON reflectance standard material in place behind the sample holder slit. The sample was measured by removing the reference standard and positioning the bonded or non-bonded measurement site directly onto the sample holder slit. Details of such measurement techniques can be found in *Applied Spectroscopy: A Compact Reference for Practitioners,* J. Workman and A. Springsteen (Eds.), Academic Press, Boston, 1998; as well as in other specialized texts on the subjects of reflectance and color measurements.

Calculations for Hunter (L*a*b*) color coordinates, Tristimulus (X, Y, Z) color coordinates, Chromaticity (x, y, z) color coordinates, and Whiteness Index (WI) were made using the Varian Instruments color calculations software. Special graphical representations (e.g.; FIGS. 1a–3b) and calculations of two- and three-dimensional appearance space differences (D) were generated using MatLab software v4.5 with command line data manipulation. The MatLab software can be obtained from The MathWorks, Inc., a business having offices at 24 Prime Park Way, Natick, Mass. 01760-1500, USA. Geometric differences (or distances) in color space were calculated using standard vector geometry where the distance (D) in two-dimensional space is given by $$D = \{(x_2 - x_1)^2 + (y_2 - y_1)^2\}^{\frac{1}{2}} \quad \text{(Equation 1)}$$

and where the distance (D) in three-dimensional space is given by $$D = \{(x_2 - x_1)^2 + (y_2 - y_1)^2 + (z_2 - z_1)^2\}^{\frac{1}{2}} \quad \text{(Equation 2)}$$

Background:

Standard color depiction utilizes graphics of Hunter L*a*b* color as a* versus b* and black versus white (L*) as separate graphic representations. For chromaticity illustration, plots of x versus y are used for conventional color space illustration. Tristimulus X, Y, and Z graphics are not typically used. These standard depictions of color do not demonstrate the sensitivity to show the dramatic appearance changes visible to the naked eye for the wet versus dry diaper samples. A key component in the dramatic appearance changes found for the diaper samples involves not only color change, but also the darkening of the sample as it becomes wet. This is due to the increased absorbance of broad regions of the visible electromagnetic spectrum for wet samples. The three testing procedures for color and appearance measurements were sensitive enough to demonstrate the visual differences for the wet versus dry samples.

Test Descriptions:

The tests enabled the appearance differences to be quantified. Each of the following test procedures may be employed to verify the appearance changes.

(1) Hunter L*a*b* color coordinates with 2° viewing angle (observer) and CIE Illuminant C—Average daylight, 6774 K (ASTM method D2244, 1987). For this test the three-dimensional Hunter a* vs. b* vs. L* color space differences were calculated (using Equation 2) for wet and dry, bonded and non-bonded areas, after accurately measuring the spectrum of each of the bonded and non-bonded areas from 400 nm to 700 nm. The spectral measurements were acquired using the method described under the Spectrum Acquisition section. Inclusion of the L* dimension for these calculations more clearly demonstrates not only the apparent color change differences, but also the blackness and whiteness effects on appearance. This single factor affected the L*a*b* difference calculations by an order of magnitude greater than the red-green (i.e., a*) or yellow-blue effects (i.e., b*). Table 1 summarizes the results of the difference calculations conducted for the particular Examples 1 through 13, which are described below in detail.

(2) Tristimulus (X, Y, Z) color coordinates with 2° viewing angle (observer) and CIE illuminant C—Average daylight, 6774 K (ASTM method E308, 1987). For this test the three-dimensional X, Y, Z color space differences were calculated (using Equation 2) for wet and dry, bonded and non-bonded areas, after accurately measuring the spectrum of each of the bonded and non-bonded areas from 400 nm to 700 nm. The spectral measurements were acquired using the method described under the Spectrum Acquisition section. Calculating the geometric differences between the data points with the three-dimensional coordinates representing: more red and more blue (i.e., X); between more green and more blue (i.e., Y), and between more blue and less blue (i.e., Z) yielded the sensitivity needed to clearly distinguish the diaper appearance. Table 2 summarizes the results of the difference calculations conducted for the particular Examples 1 through 8, which are described below in detail.

(3) Chromaticity (x, y, z) color coordinates with 2° viewing angle (observer) and CIE illuminant C—Average daylight, 6774 K (ASTM method E308, 1987; CIE publication number 15.2, 1986; and ASTM method D2244, 1987); combined with WI (i.e., Whiteness Index as described in ASTM method E313) using CIE source C and the 2° standard observer. For this combination of tests the two-dimensional x vs. WI appearance space differences were calculated (using Equation 1) for wet and dry, bonded and non-bonded areas, after accurately measuring the spectrum of each of the bonded and non-bonded areas from 400 nm to 700 nm. The spectral measurements were acquired using the method described under the Spectrum Acquisition section. Calculating the geometric differences between more red and more blue (i.e., x); and between lighter and darker (i.e., WI) yielded the greatest sensitivity test to clearly distinguish the diaper appearance. Table 3 summarizes the results of the difference calculations conducted for the particular Examples 1 through 8, which are described below in detail.

Note: CIE indicates the Commission Internationale de l'Eclairage, or the International Color Commission standard methods. Observer angle for measurements (i.e., 2° and 10°), and Illuminant C are defined in CIE publication No. 15.2, 1986.

The following examples are presented to provide a more detailed understanding of the invention. The examples are representative and are not intended to limit the scope of the invention.

EXAMPLES

Example 1

The composite material of Example 1 included an underlying layer of blue-colored forming tissue, and an overlying, breathable, cloth-like outer cover. The material was obtained from a boy's disposable diaper.

The blue forming tissue was a 20 $g/m^2$ basis weight, low porosity, wet strength, creped wadding made from a 50% hardwood/50% softwood furnish. The Hunter color targets of the tissue, minimum and maximum, were as follows:

| Blue Forming Tissue: | Target | Min | Max |
|---|---|---|---|
| Rd: | 55 | 52 | 58 |
| a: | −7 | −10 | −4 |
| b: | −2 | −23 | −17 |

The outer cover material was referred to as LLDPE-BSTL, and included of a Breathable Stretch Thermal Laminate made with a Linear Low Density PolyEthlyene film. More particularly, the air-permeable, outer cover material included a 17 $g/m^2$ (0.5 osy) 2 dpf (denier per fiber) polypropylene spunbond nonwoven fabric which was laminated, and thermally bonded along a pattern of discrete bonding areas to a breathable, stretch-thinned, 17 gsm (0.5 osy), cast multi-layer polyethylene based film. The film was an A-B-A layered film, where the A-layer was an EVA (Ethyl Vinyl Alcohol) and the B-layer was a core layer composed of 50% $CaCO_3$ and 50% LLDPE. The nonwoven fabric formed the outermost surface of the sample.

Sample 1A was composed of a non-bonded region of the composite material provided by Example 1. The tested sample represented a non-bonded area of approximately 1.5 mm wide by 25 mm long, in its condition following the saline wetting of the material of Example 1, and measured in reflectance, as observed from the nonwoven fabric side of the sample, in the manner described previously.

Sample 1B was composed of a bonded area of the composite material described in Example 1. The tested sample represented a bonded area of approximately 1.5 mm wide by 25 mm long, in its condition following the saline wetting of the material of Example 1, and measured in reflectance, as described previously.

Sample 1C was composed a non-bonded area of the composite material of Example 1. The tested sample represents a non-bonded area of approximately 1.5 mm wide by 25 mm long of the dry material of Example 1, prior to saline wetting and measured in reflectance, as described previously.

Sample 1D was composed a bonded area of the composite material Example 1. The tested sample represented a bonded area of approximately 1.5 mm wide by 25 mm long of the dry material of Example 1, prior to saline wetting and measured in reflectance, as described previously.

Example 2

The composite material of Example 2 included an underlying layer of white-colored forming tissue and an overlying, breathable outer cover material. The composite material was obtained from a boy's disposable diaper.

The white forming tissue was a 20 g/m² basis weight, low porosity, wet strength, creped wadding made from a 50% hardwood/50% softwood furnish. The outer cover was composed of the outer cover material described in Example 1. The nonwoven fabric formed the outermost surface of the sample.

Sample 2A was composed of a non-bonded region of the composite material provided by Example 2. The tested sample represented a non-bonded area of approximately 1.5 mm wide by 25 mm long, in its condition following the saline wetting of the material of Example 2, and measured in reflectance, as observed from the nonwoven fabric side of the sample, in the manner described previously.

Sample 2B was composed of a bonded area of the composite material described in Example 2. The tested sample represented a bonded area of approximately 1.5 mm wide by 25 mm long, in its condition following the saline wetting of the material of Example 2, and measured in reflectance, as described previously.

Sample 2C was composed a non-bonded area of the composite material of Example 2. The tested sample represents a non-bonded area of approximately 1.5 mm wide by 25 mm long of the dry material of Example 2, prior to saline wetting and measured in reflectance, as described previously.

Sample 2D was composed a bonded area of the composite material Example 2. The tested sample represented a bonded area of approximately 1.5 mm wide by 25 mm long of the dry material of Example 2, prior to saline wetting and measured in reflectance, as described previously.

Example 3

The composite material of Example 3 included an underlying layer of white colored forming tissue material, combined with an overlying, non-breathable outer cover material. The material was obtained from a boy's ULTRATRIM disposable diaper manufactured by Kimberly-Clark Corporation.

The layer of white colored forming tissue was composed of 20 g/m² basis weight, low porosity, wet strength, creped wadding made from a 50% hardwood/50% softwood furnish. The non-breathable outer cover material was a low-cost cloth-like laminate composed of a 17 g/m² (0.5 osy) basis weight, 2 dpf (denier per fiber) polypropylene spunbond, nonwoven fabric, which was laminated and thermally bonded along a pattern of discrete bonding areas to a non-breathable, stretch-thinned film having a film basis weight of about 10 g/m² (0.29 osy). The film was an A-B-C film where the A-layer was polypropylene, the B-layer was polypropylene with TiO2 layer, and the C-layer was a polypropylene layer with a catalloy. The nonwoven fabric formed the outermost surface of the sample.

Sample 3A was composed of a non-bonded region of the composite material provided by Example 3. The tested sample represented a non-bonded area of approximately 1.5 mm wide by 25 mm long, in its condition following the saline wetting of the material of Example 3, and measured in reflectance, as observed from the nonwoven fabric side of the sample, in the manner described previously.

Sample 3B was composed of a bonded area of the composite material described in Example 3. The tested sample represented a bonded area of approximately 1.5 mm wide by 25 mm long, in its condition following the saline wetting of the material of Example 3, and measured in reflectance, as described previously.

Sample 3C was composed a non-bonded area of the composite material of Example 3. The tested sample represents a non-bonded area of approximately 1.5 mm wide by 25 mm long of the dry material of Example 3, prior to saline wetting and measured in reflectance, as described previously.

Sample 3D was composed a bonded area of the composite material Example 3. The tested sample represented a bonded area of approximately 1.5 mm wide by 25 mm long of the dry material of Example 3, prior to saline wetting and measured in reflectance, as described previously.

Example 4

The composite material of Example 4 included an underlying layer of whiter forming tissue material, and an overlying, breathable outer cover material. The material was obtained from a boy's ULTRATRIM disposable diaper manufactured by Kimberly-Clark Corporation.

The layer of white colored forming tissue was composed of 20 g/m² basis weight, low porosity, wet strength, creped wadding made from a 50% hardwood/50% softwood furnish. The breathable outer cover was referred to as a BSTL-PP, and was a Breathable Stretch Thermal Laminate made with a PolyPropolyene film. More particularly, the breathable outer cover material included a 17 g/m² (0.5 osy) basis weight, 2 dpf (denier per fiber) polypropylene spunbond nonwoven fabric, which was laminated and thermally bonded along a pattern of discrete bonding areas to a breathable, stretch-thinned, 17 g/m² (0.5 osy) basis weight, cast multi-layer polypropylene based film. The film was an A-B-A layered film where the A-layer was EVA (Ethyl Vinyl Alcohol), the B-layer was a core layer composed of 50% Ca CO3 and 50% PP. The nonwoven fabric formed the outermost surface of the sample.

Sample 4A was composed of a non-bonded region of the composite material provided by Example 4. The tested sample represented a non-bonded area of approximately 1.5 mm wide by 25 mm long, in its condition following the saline wetting of the material of Example 4, and measured in reflectance, as observed from the nonwoven fabric side of the sample, in the manner described previously.

Sample 4B was composed of a bonded area of the composite material described in Example 4. The tested sample represented a bonded area of approximately 1.5 mm wide by 25 mm long, in its condition following the saline wetting of the material of Example 4, and measured in reflectance, as described previously.

Sample 4C was composed a non-bonded area of the composite material of Example 4. The tested sample represents a non-bonded area of approximately 1.5 mm wide by 25 mm long of the dry material of Example 4, prior to saline wetting and measured in reflectance, as described previously.

Sample 4D was composed a bonded area of the composite material Example 4. The tested sample represented a bonded area of approximately 1.5 mm wide by 25 mm long of the dry material of Example 4, prior to saline wetting and measured in reflectance, as described previously.

Example 5

The composite material of Example 5 included a layer of pink-colored forming tissue, and a breathable, cloth-like outer cover. The material was obtained from a girl's disposable diaper.

The pink forming tissue was a 20 g/m² basis weight, low porosity, wet strength, creped wadding made from a 50% hardwood/50% softwood furnish. The Hunter color targets, minimum and maximum were as follows:

| Pink forming tissue: | Target | Min | Max |
| --- | --- | --- | --- |
| Rd | 66 | 62 | 70 |
| a | 21 | 16 | 25 |
| b | 0 | −4 | +4 |

The outer cover material was the LLDPE-BSTL, nonwoven fabric and film, laminate material of Example 1. The nonwoven fabric formed the outermost surface of the sample.

Sample 5A was composed of a non-bonded region of the composite material provided by Example 5. The tested sample represented a non-bonded area of approximately 1.5 mm wide by 25 mm long, in its condition following the saline wetting of the material of Example 5, and measured in reflectance, as observed from the nonwoven fabric side of the sample, in the manner described previously.

Sample 5B was composed of a bonded area of the composite material described in Example 5. The tested sample represented a bonded area of approximately 1.5 mm wide by 25 mm long, in its condition following the saline wetting of the material of Example 5, and measured in reflectance, as described previously.

Sample 5C was composed a non-bonded area of the composite material of Example 5. The tested sample represents a non-bonded area of approximately 1.5 mm wide by 25 mm long of the dry material of Example 5, prior to saline wetting and measured in reflectance, as described previously.

Sample 5D was composed a bonded area of the composite material Example 5. The tested sample represented a bonded area of approximately 1.5 mm wide by 25 mm long of the dry material of Example 5, prior to saline wetting and measured in reflectance, as described previously.

Example 6

The composite material of Example 6 included a layer of white-colored forming tissue and a breathable outer cover material. The composite material was obtained from a girl's disposable diaper.

The white forming tissue was a 20 g/m² basis weight, low porosity, wet strength, creped wadding made from a 50% hardwood/50% softwood furnish. The outer cover was a BSTL-LLDPE material, and was composed of the outer cover material described in Example 1. The nonwoven fabric formed the outermost surface of the sample.

Sample 6A was composed of a non-bonded region of the composite material provided by Example 6. The tested sample represented a non-bonded area of approximately 1.5 mm wide by 25 mm long, in its condition following the saline wetting of the material of Example 6, and measured in reflectance, as observed from the nonwoven fabric side of the sample, in the manner described previously.

Sample 6B was composed of a bonded area of the composite material described in Example 6. The tested sample represented a bonded area of approximately 1.5 mm wide by 25 mm long, in its condition following the saline wetting of the material of Example 6, and measured in reflectance, as described previously.

Sample 6C was composed a non-bonded area of the composite material of Example 6. The tested sample represents a non-bonded area of approximately 1.5 mm wide by 25 mm long of the dry material of Example 6, prior to saline wetting and measured in reflectance, as described previously.

Sample 6D was composed a bonded area of the composite material Example 6. The tested sample represented a bonded area of approximately 1.5 mm wide by 25 mm long of the dry material of Example 6, prior to saline wetting and measured in reflectance, as described previously.

Example 7

The composite material of Example 7 included a layer of white forming tissue material, and a non-breathable outer cover material. The material was obtained from a girl's ULTRATRIM disposable diaper manufactured by Kimberly-Clark Corporation.

The layer of white colored forming tissue was composed of 20 g/m² basis weight, low porosity, wet strength, creped wadding made from a 50% hardwood/50% softwood furnish. The non-breathable outer cover material was the low-cost cloth-like laminate of Example 3. The nonwoven fabric formed the outermost surface of the sample.

Sample 7A was composed of a non-bonded region of the composite material provided by Example 7. The tested sample represented a non-bonded area of approximately 1.5 mm wide by 25 mm long, in its condition following the saline wetting of the material of Example 7, and measured in reflectance, as observed from the nonwoven fabric side of the sample, in the manner described previously.

Sample 7B was composed of a bonded area of the composite material described in Example 7. The tested sample represented a bonded area of approximately 1.5 mm wide by 25 mm long, in its condition following the saline wetting of the material of Example 7, and measured in reflectance, as described previously.

Sample 7C was composed a non-bonded area of the composite material of Example 7. The tested sample represents a non-bonded area of approximately 1.5 mm wide by 25 mm long of the dry material of Example 7, prior to saline wetting and measured in reflectance, as described previously.

Sample 7D was composed a bonded area of the composite material Example 7. The tested sample represented a bonded area of approximately 1.5 mm wide by 25 mm long of the dry material of Example 7, prior to saline wetting and measured in reflectance, as described previously.

Example 8

The composite material of Example 4 included a layer of white forming tissue material, and a breathable outer cover material. The material was obtained from a girl's ULTRATRIM disposable diaper manufactured by Kimberly-Clark Corporation.

The layer of white colored forming tissue was composed of 20 g/m² basis weight, low porosity, wet strength, creped wadding made from a 50% hardwood/50% softwood furnish. The breathable outer cover was referred to as a BSTL-PP, and was the breathable outer cover material of Example 4. The nonwoven fabric formed the outermost surface of the sample.

Sample 8A was composed of a non-bonded region of the composite material provided by Example 8. The tested sample represented a non-bonded area of approximately 1.5 mm wide by 25 mm long, in its condition following the saline wetting of the material of Example 8, and measured in reflectance, as observed from the nonwoven fabric side of the sample, in the manner described previously.

Sample 8B was composed of a bonded area of the composite material described in Example 8. The tested sample represented a bonded area of approximately 1.5 mm wide by 25 mm long, in its condition following the saline wetting of the material of Example 8, and measured in reflectance, as described previously.

Sample 8C was composed a non-bonded area of the composite material of Example 8. The tested sample represents a non-bonded area of approximately 1.5 mm wide by 25 mm long of the dry material of Example 8, prior to saline wetting and measured in reflectance, as described previously.

Sample 8D was composed a bonded area of the composite material Example 8. The tested sample represented a bonded area of approximately 1.5 mm wide by 25 mm long of the dry material of Example 8, prior to saline wetting and measured in reflectance, as described previously.

Example Calculation

The following representative calculation is presented to provide a further understanding of the invention:

Sample 1A had the following corresponding data:
Hunter ($L^*a^*b^*$): L=81.7794; a=-0.9223; b=-2.4534
Tristimulus (X, Y, Z): X=65.1667; Y=66.8787; Z=82.4562
Chromaticity (x): 0.3038
Whiteness Index: 78.7256

Sample 1B had the following corresponding data:
Hunter ($L^*a^*b^*$): L=79.2616; a=-0.8856; b=-2.8657
Tristimulus (X, Y, Z): X=61.2194; Y=62.8239; Z=78.1101
Chromaticity (x): 0.3028
Whiteness Index: 76.1651

Sample 1C had the following corresponding data:
Hunter ($L^*a^*b^*$): L=94.2059; a=-1.2625; b=-1.4908
Tristimulus (X, Y, Z): X=86.3701; Y=88.7476; Z=107.2942
Chromaticity (x): 0.3058
Whiteness Index: 97.2700

Sample 1D had the following corresponding data:
Hunter ($L^*a^*b^*$): L=94.7681; a=-1.3867; b=-1.6569
Tristimulus (X, Y, Z): X=87.3421; Y=89.8100; Z=108.8302
Chromaticity (x): 0.3054
Whiteness Index: 99.2867

Similar, corresponding data were obtained for each of the other Examples 2 through 8.

A representative example of the calculations conducted with the data from Example 1 is as follows:

The Hunter $L^*a^*b^*$ Three-dimensional Space Difference (D) is calculated by using Equation 2 shown in the previous section, and substituting the values representing the sample measurements for Hunter $L^*a^*b^*$ as follows:

For the Sample 1A difference from Sample 1B (wet samples):

$$D=[(81.7794-79.2616)^2+(-0.9223+0.8856)^2+(-2.4534+2.8657)^2]^{1/2}=2.55$$

For the Sample 1C difference from Sample 1D (dry samples):

$$D=[(94.2059-94.7681)^2+(-1.2625+1.3867)^2+(-1.4908+1.6569)^2]^{1/2}=0.60$$

The Hunter $L^*a^*b^*$ Contrast Ratio (Wet/Dry) for the Three-dimensional Space Difference (D) is calculated by dividing the D value calculated for the wet samples (Samples 1A and 1B) by the D value calculated for the dry samples (Samples 1C and 1D). The calculation of the Contrast Ratio for the above example is given as 2.55/0.60=4.25.

The Tristimulus X, Y, Z Three-dimensional Space Difference (D) is calculated by using equation 2 shown in the previous section, and substituting the values representing the sample measurements for Tristimulus X, Y, Z, as follows:

For the Sample 1A difference from Sample 1B (wet samples):

$$D=[(65.1667-61.2194)^2+(66.8787-62.8239)^2+(82.4562-78.1101)^2]^{1/2}=7.14$$

For the Sample 1C difference from Sample 1D (dry samples):

$$D=[(86.3701-87.3421)^2+(88.7476-89.8100)^2+(107.2942-108.8302)^2]^{1/2}=2.11$$

The Tristimulus X, Y, Z Contrast Ratio (Wet/Dry) for the Three-dimensional Space Difference (D) is calculated by dividing the D value calculated for the wet samples (Samples 1A and 1B) the D value calculated for the dry samples (Samples 1C and 1D). The Contrast Ratio for the above example is given as 7.14/2.11=3.38.

The Chromaticity x, Whiteness Index (WI) Two-dimensional Space Difference (D) is calculated by using equation I shown in the previous section, and substituting the values representing the sample measurements for Chromaticity (x) and Whiteness Index (WI) as follows:

For the Sample 1A difference from Sample 1B (wet samples):

$$D=[(0.3038-0.3028)^2+(78.7256-76.1651)^2]^{1/2}=2.56$$

For the Sample 1C difference from Sample 1D (dry samples):

$$D=[(0.3058-0.3054)^2+(97.2700-99.2867)^2]^{1/2}=2.02$$

The Chromaticity (x), Whiteness Index (WI) Contrast Ratio (Wet/Dry) for the Two-dimensional Space Difference (D) is calculated by dividing the D value calculated for the wet samples (Samples 1A and 1B) by the D value calculated for the dry samples (Samples 1C and 1D). The Contrast Ratio for the above example is given as 2.56/2.02=1.27.

Table 1 summarizes the results of the $L^*a^*b^*$ difference calculations. Table 2 summarizes the results of the Tristimulus (X, Y, Z) difference calculations. Table 3 summarizes the results the difference calculations for Chromaticity (x, y, z) combined with Whiteness Index.

DIFFERENCE (D) CALCULATIONS TABLES:

TABLE 1

Hunter $L^*a^*b^*$ Three-dimensional Space Differences (D)

| Sample No. | Samples Used for D calculations | Difference (D)[a] | Contrast Ratio (Wet/Dry)[b] |
|---|---|---|---|
| 1 | 1A–1B | 2.55 | |
|   | 1C–1D | 0.60 | 4.25 |
| 2 | 2A–2B | 3.64 | |
|   | 2C–2D | 0.42 | 8.67 |

TABLE 1-continued

Hunter L*a*b* Three-dimensional Space Differences (D)

| Sample No. | Samples Used for D calculations | Difference (D)[a] | Contrast Ratio (Wet/Dry)[b] |
|---|---|---|---|
| 3 | 3A–3B | 2.64 | |
|   | 3C–3D | 7.79 | 0.34 |
| 4 | 4A–4B | 0.89 | |
|   | 4C–4D | 0.10 | 0.11 |
| 5 | 5A–5B | 3.36 | |
|   | 5C–5D | 1.06 | 3.17 |
| 6 | 6A–6B | 2.01 | |
|   | 6C–6D | 0.18 | 11.17 |
| 7 | 7A–7B | 0.66 | |
|   | 7C–7D | 1.54 | 0.43 |
| 8 | 8A–8B | 2.63 | |
|   | 8C–8D | 2.98 | 1.13 |

[a]Calculated difference in appearance space using test data and Equation 2.
[b]Indicates the ratios of the distances in appearance space (i.e., contrast) between non-bonded and bonded areas for wet versus dry conditions.

Figure 8:
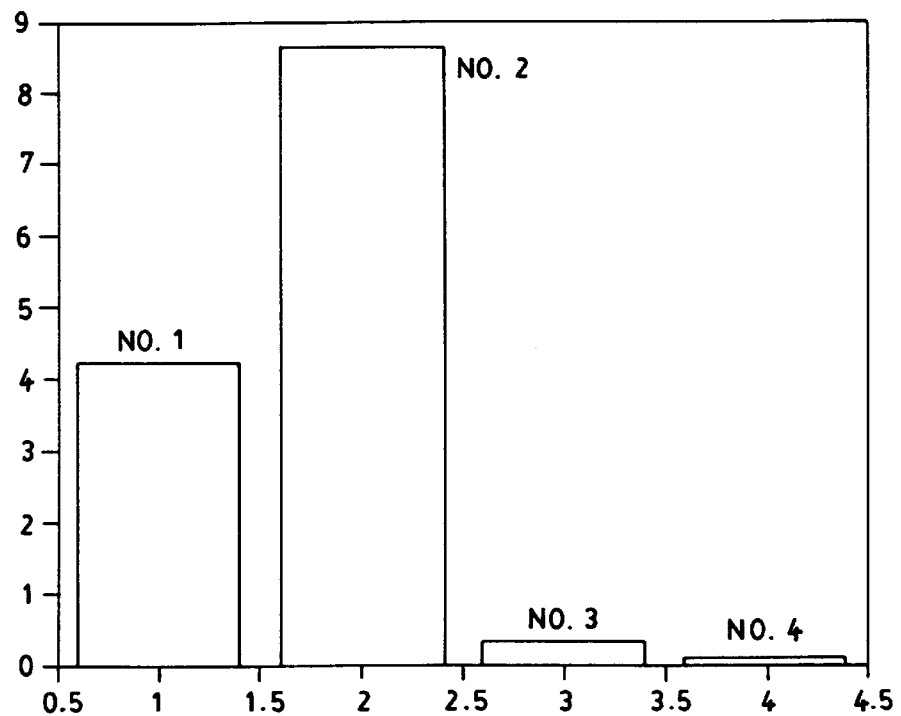
FIG. 8 is a graph which representatively shows a comparison of the Hunter color Contrast Ratios (wet versus dry) for a first group of sample materials.

FIG. 8 shows a comparison of the Hunter color Contrast Ratios (wet versus dry) for Sample 1 through Sample 4.

Figure 8A:
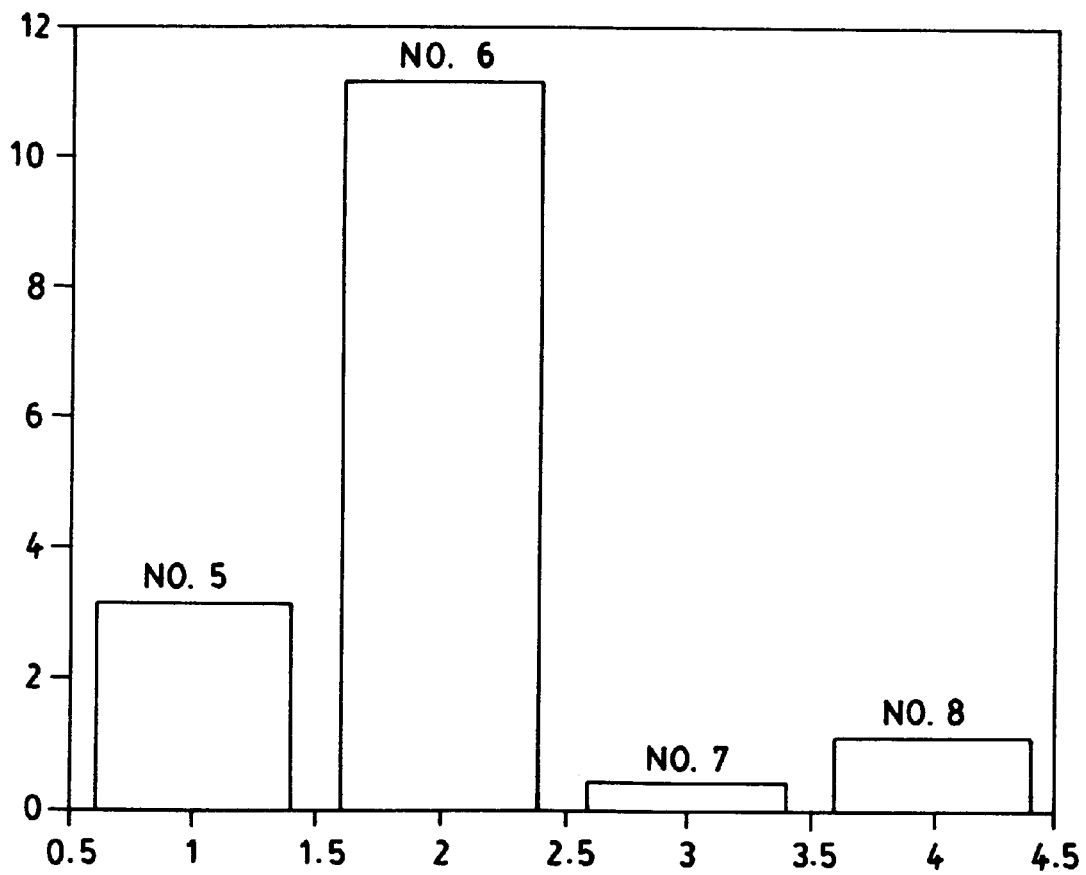
FIG. 8A is a graph which representatively shows comparison of the Hunter color Contrast Ratios (wet versus dry) for a second group of sample materials.

FIG. 8A shows a comparison of the Hunter color Contrast Ratios (wet versus dry) for Sample 5 through Sample 8.

TABLE 2

Tristimulus X, Y, Z Three-dimensional Space Differences (D)

| Sample No. | Samples Used for D calculations | Difference (D)[a] | Contrast Ratio (Wet/Dry)[b] |
|---|---|---|---|
| 1 | 1A–1B | 7.14 | |
|   | 1C–1D | 2.11 | 3.38 |
| 2 | 2A–2B | 11.16 | |
|   | 2C–2D | 1.40 | 7.97 |
| 3 | 3A–3B | 8.45 | |
|   | 3C–3D | 26.8 | 0.32 |
| 4 | 4A–4B | 3.05 | |
|   | 4C–4D | 0.12 | 0.04 |
| 5 | 5A–5B | 9.67 | |
|   | 5C–5D | 3.10 | 3.12 |
| 6 | 6A–6B | 5.81 | |
|   | 6C–6D | 0.31 | 18.74 |
| 7 | 7A–7B | 1.72 | |
|   | 7C–7D | 3.40 | 0.51 |
| 8 | 8A–8B | 8.63 | |
|   | 8C–8D | 9.08 | 1.05 |

[a]Calculated difference in appearance space using test data and Equation 2.
[b]Indicates the ratios of the distances in appearance space (i.e., contrast) between non-bonded and bonded areas for wet versus dry conditions.

Figure 9:
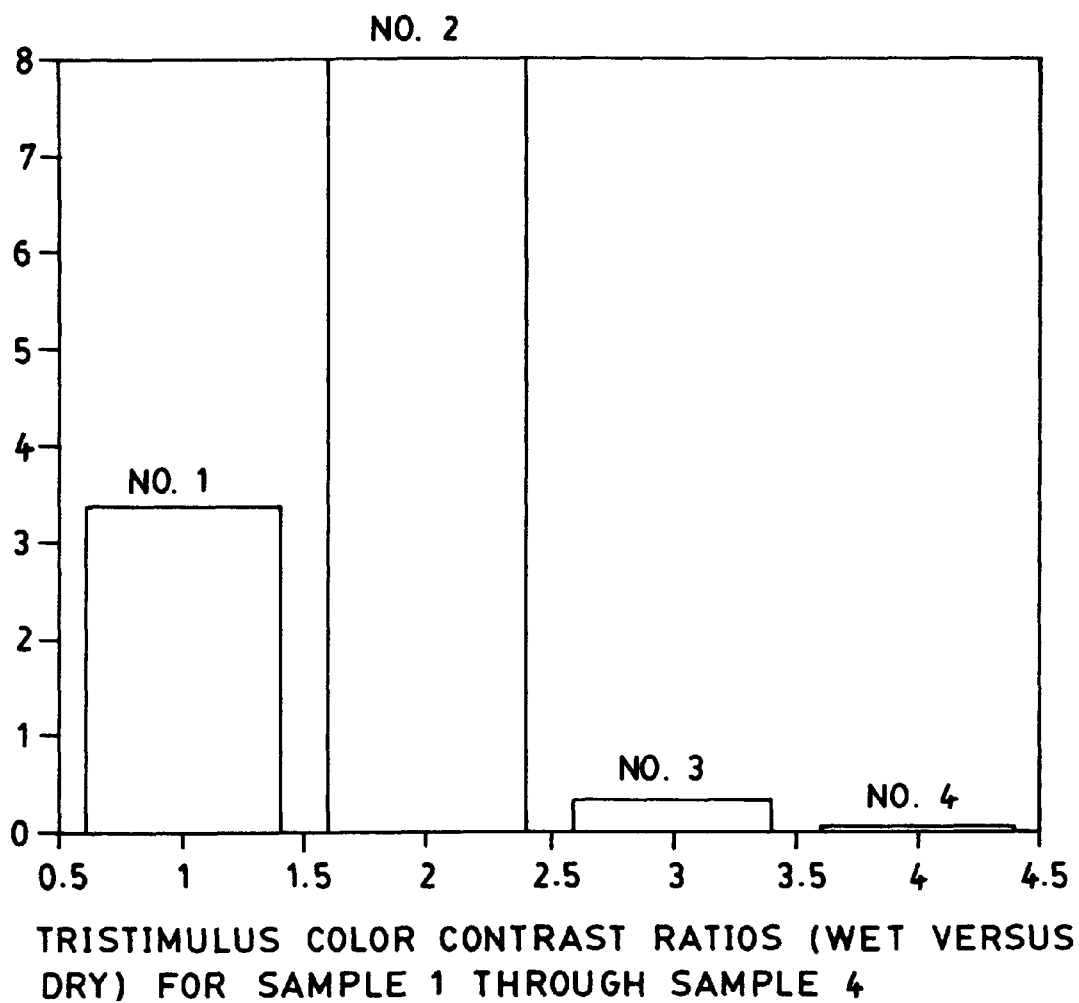
FIG. 9 is a graph which representatively shows a comparison of the Tristimulus color Contrast Ratios (wet versus dry) for a first group of sample materials.

FIG. 9 shows a comparison of the Tristimulus color Contrast Ratios (wet versus dry) for Sample 1 through Sample 4.

Figure 9A:
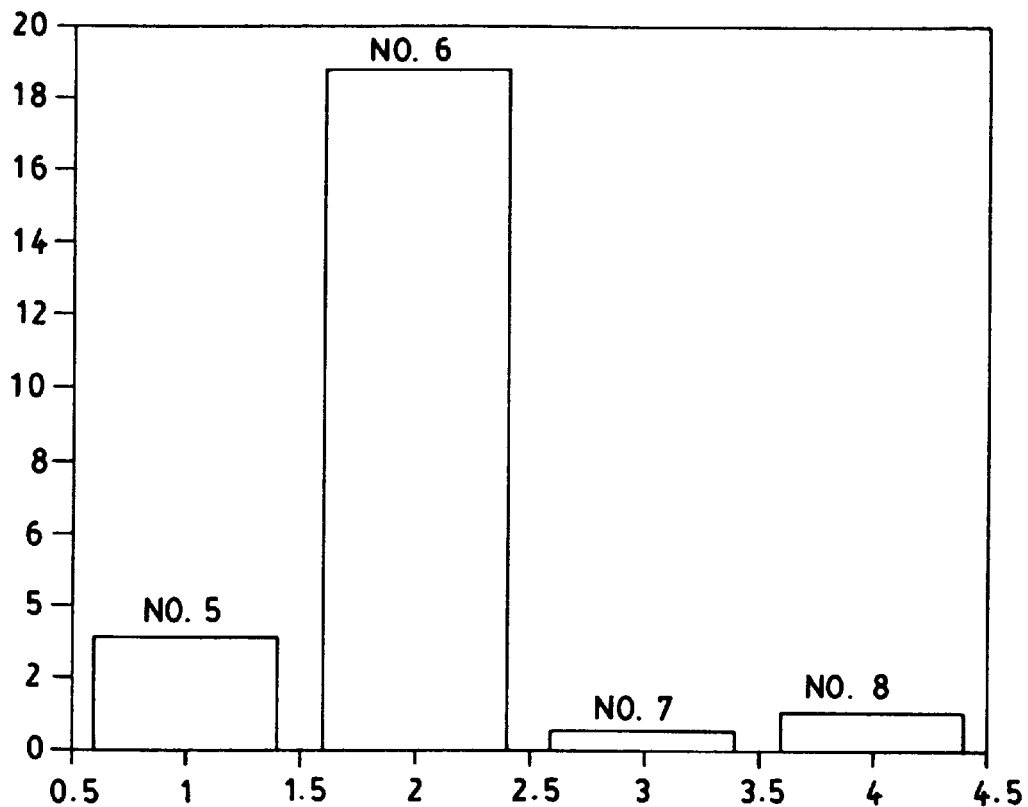
FIG. 9A is a graph which representatively shows a comparison of the Tristimulus color Contrast Ratios (wet versus dry) for a second group of sample materials.

FIG. 9A shows a comparison of the Tristimulus color Contrast Ratios (wet versus dry) for Sample 5 through Sample 8.

TABLE 3

Chromaticity x, WI Two-dimensional Space Differences (D)

| Sample No. | Samples Used for D calculations | Difference (D)[a] | Contrast Ratio (Wet/Dry)[b] |
|---|---|---|---|
| 1 | 1A–1B | 2.56 | |
|   | 1C–1D | 2.02 | 1.27 |
| 2 | 2A–2B | 4.43 | |
|   | 2C–2D | 1.26 | 3.52 |

TABLE 3-continued

Chromaticity x, WI Two-dimensional Space Differences (D)

| Sample No. | Samples Used for D calculations | Difference (D)[a] | Contrast Ratio (Wet/Dry)[b] |
|---|---|---|---|
| 3 | 3A–3B | 3.38 | |
|   | 3C–3D | 13.71 | 0.25 |
| 4 | 4A–4B | 1.24 | |
|   | 4C–4D | 0.41 | 0.33 |
| 5 | 5A–5B | 3.86 | |
|   | 5C–5D | 0.66 | 5.85 |
| 6 | 6A–6B | 1.80 | |
|   | 6C–6D | 0.17 | 10.59 |
| 7 | 7A–7B | 0.18 | |
|   | 7C–7D | 1.02 | 0.18 |
| 8 | 8A–8B | 2.23 | |
|   | 8C–8D | 2.41 | 1.08 |

[a]Calculated difference in appearance space using test data and Equation 2.
[b]Indicates the ratios of the distances in appearance space (i.e., contrast) between non-bonded and bonded areas for wet versus dry conditions.

Figure 10:
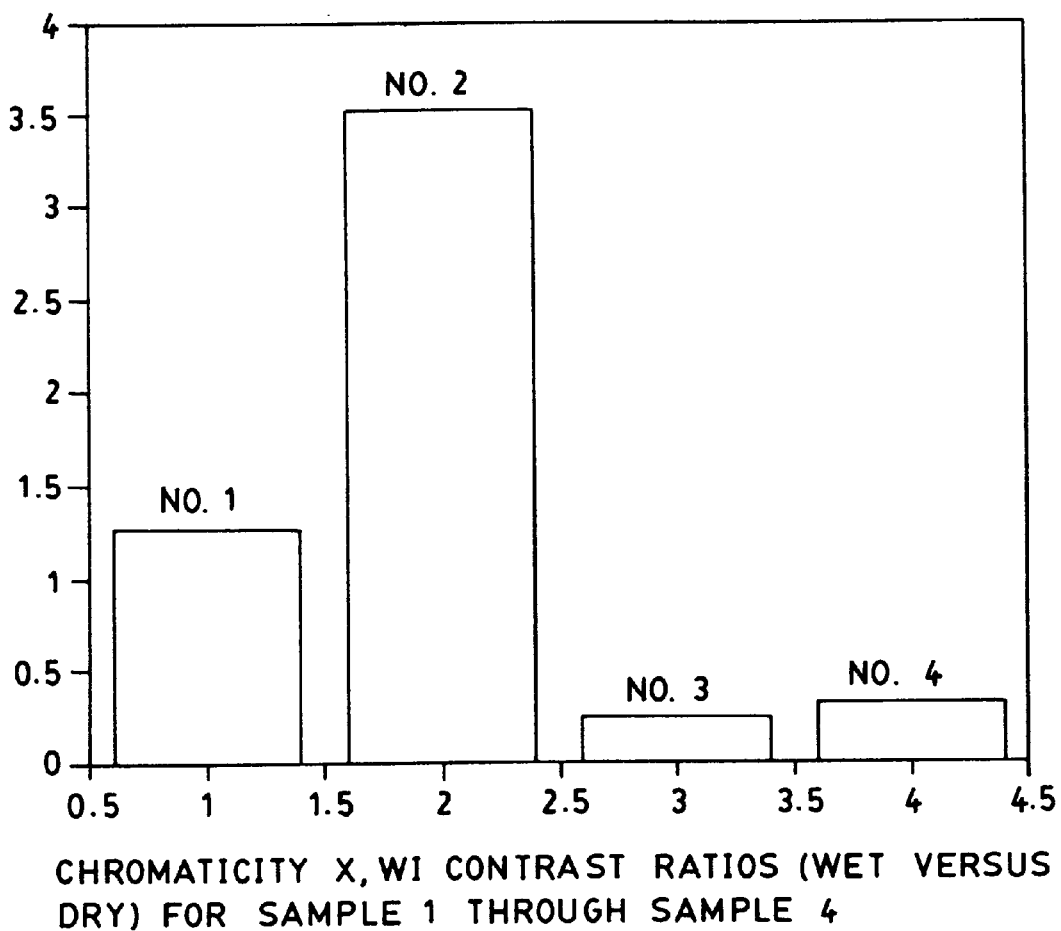
FIG. 10 is a graph which representatively shows a comparison of the Chromaticity x, WI Contrast Ratios (wet versus dry) for a first group of sample materials.

FIG. 10 shows a comparison of the Chromaticity x, WI Contrast Ratios (wet versus dry) for Sample 1 through Sample 4.

Figure 10A:
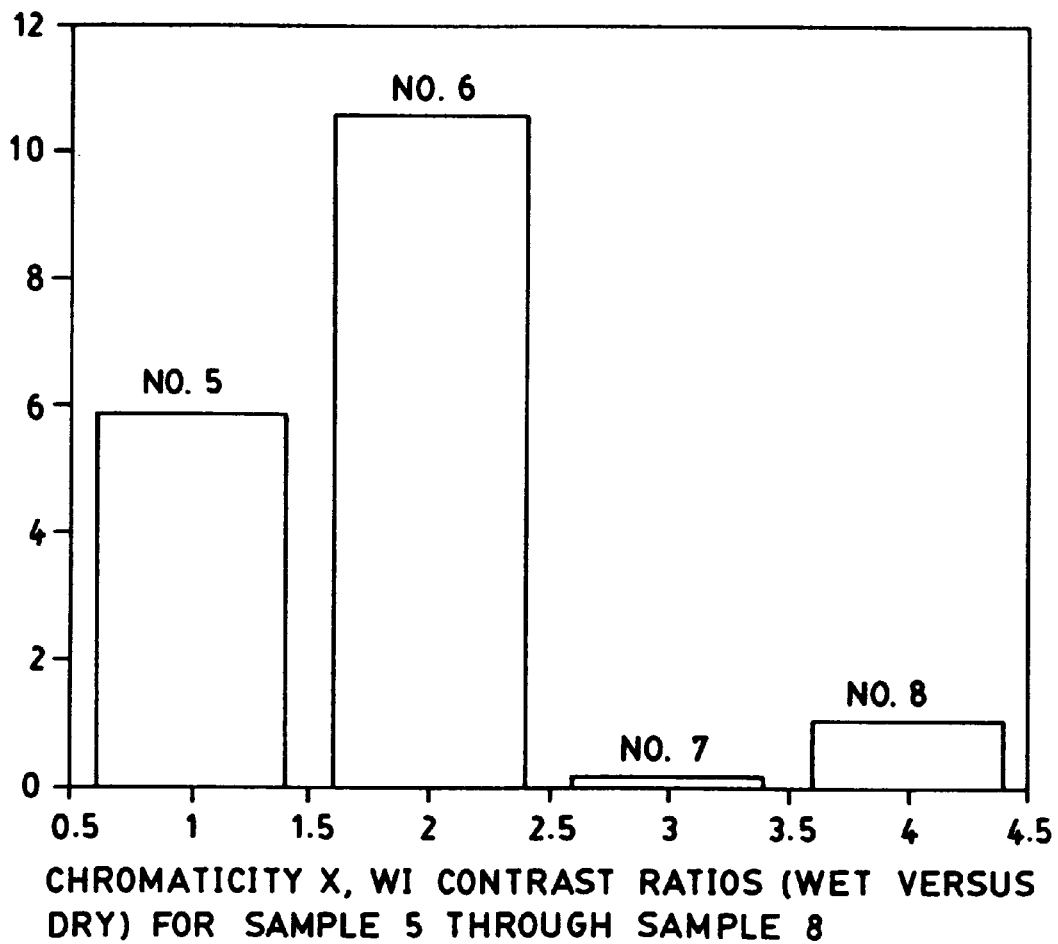
FIG. 10A is a graph which representatively shows a comparison of the Chromaticity x, WI Contrast Ratios (wet versus dry) for a second group of sample materials.

FIG 10A shows a comparison of the Chromaticity x, WI Contrast Ratios (wet versus dry) for Sample 5 through Sample 8.

Results Summary:

Table 1 through 3 and FIGS. 8 through 10B show the results of the data comparison methods conducted on the Examples. The Hunter L*a*b* three-dimensional color differences, Tristimulus (X, Y, Z) color differences, and Chromaticity (x) versus Whiteness Index (WI) differences provided sensitive tests in detecting color and appearance changes between diaper samples. The fourth column of each of the Tables 1–3 indicates the ratios of the distances in appearance space for each of the three tests (i.e., appearance contrast) between non-bonded and bonded areas for the wet versus dry conditions. The larger the ratio value the greater is the change in appearance (or appearance contrast) due to wetness, indicating that bonded and non-bonded areas appear more different (i.e., have greater contrast) as a result of the wetting process. A ratio of less than one indicates that there is more contrast between bonded and non-bonded areas for the dry condition as compared to the wet, so that the bonded and non-bonded areas for the wet diaper appear more alike (i.e., exhibit less contrast) than the dry diaper.

Having described the invention in rather full detail, it will be readily apparent that various changes and modifications can be made without departing from the spirit of the invention. All of such changes and modifications are contemplated as being within the scope of the invention as defined by the subjoined claims.

What is claimed is:

1. An absorbent article having a front waistband portion, a back waistband portion and an intermediate portion, said article comprising:

a flexible and readily conformable backsheet member;

a liquid permeable topsheet layer;

an absorbent body having a retention portion sandwiched between said backsheet member and said topsheet layer; and a wetness indicator for visually showing a presence of liquid in selected regions of said article, said wetness indicator including;

at least one indicator section of said backsheet member which includes a backsheet laminate material having a fibrous nonwoven web attached to a polymer sheet layer, said polymer sheet layer composed of a linear-low-density-polyethylene material, said indicator section of said backsheet member including a plurality of translucent windows which are arranged in an area pattern and are formed by a selected thermal bonding of said fibrous nonwoven web to said polymer sheet layer in said backsheet laminate material, and a layer of contrast material attached to said article at an operative location which is interposed between an intended wearer of the article and said indicator section of the backsheet member, said contrast layer having a first appearance through said translucent windows when said contrast material is dry, and having a visually different second appearance through said translucent windows when said contrast material is wetted with water, wherein said indicator section provides a Contrast Ratio of at least about 1.3, as determined with Hunter L*a*b* values.

2. An article as recited in claim 1, wherein said backsheet member is breathable.

3. An article as recited in claim 2, wherein said backsheet member provides a WVTR value of not less than about 500 g/m$^2$ per 24 hr.

4. An article as recited in claim 1, wherein said fibrous nonwoven web of said indicator section is composed of polypropylene fibers.

5. An article as recited in claim 1, wherein said translucent windows are formed by a sonic bonding of said fibrous nonwoven web to said polymer layer in said backsheet laminate material.

6. An article as recited in claim 1, wherein said layer of contrast material is interposed between said indicator section of said backsheet member and said retention portion.

7. An article as recited in claim 1, wherein said layer of contrast material is interposed between said topsheet layer and said retention portion.

8. An article as recited in claim 1, wherein each translucent window has a window height of at least about 0.01 inch.

9. An article as recited in claim 1, wherein each translucent window has a window length of at least about 0.0625 inch.

10. An article as recited in claim 1, wherein said bonding of said polymer sheet layer to said nonwoven web provides a total bonding area which is at least about 11% of an overall area of said backsheet member.

11. An article as recited in claim 1, wherein said bonding of said polymer sheet layer to said nonwoven web provides a total translucent window area which is at least about 11% of an overall area of the indicator section of the backsheet member.

12. An article as recited in claim 1, wherein at least a portion of the wetness indicator is located in at least a crotch section of the article.

13. An article as recited in claim 1, wherein said indicator section of the backsheet member has an indicator length which extends longitudinally from the crotch section of the diaper up to a line which is not less than about 3 cm from a longitudinally terminal edge of said front waistband portion.

14. An article as recited in claim 1, wherein said indicator section of the backsheet member has an indicator length which extends longitudinally from the crotch section of the diaper up to a line which is not less than about 3 cm from a longitudinally terminal edge of said back waistband portion.

15. An article as recited in claim 1, wherein said indicator section of the backsheet member has an indicator length which extends longitudinally from the crotch section of the diaper up to a line which is not less than about 10 cm from a longitudinally terminal edge of said front waistband portion.

16. An absorbent article as recited in claim 1, wherein said indicator section provides a Contrast Ratio of at least about 2.

17. An absorbent article as recited in claim 1, wherein said indicator section provides a Contrast Ratio of at least about 3.

18. An absorbent article as recited in claim 1, wherein said polymer sheet layer includes a core layer sandwiched between skin layers, and said core layer includes said linear-low-density-polyethylene material.

19. An absorbent article as recited in claim 18, wherein at least one said skin layer is compatible with said nonwoven layer and said core layer, and attaches to said fibrous nonwoven layer upon an application of heat and pressure.

20. An absorbent article as recited in claim 19, wherein said at least one skin layer provides a meltable intermediary between said core layer and said fibrous nonwoven layer.

21. An absorbent article having a front waistband portion, a back waistband portion and an intermediate portion, said article comprising:

a flexible and readily conformable backsheet member;

a liquid permeable topsheet layer;

an absorbent body having a retention portion and sandwiched between said backsheet member and said topsheet layer; and a wetness indicator for visually showing a presence of liquid in selected regions of said article, said wetness indicator including;

at least one indicator section of said backsheet member which includes a backsheet material having a polymer sheet layer, said indicator section of said backsheet member including a plurality of translucent windows which are arranged in an area pattern and are formed by a selected thermal treatment of said polymer sheet layer; and said indicator section having a first appearance when portions of said article at the translucent windows are dry, and having a visually different second appearance when portions of said article at the translucent windows are wetted with water, said indicator section thereby providing a Contrast Ratio of at least about 1.3, as determined with Hunter L*a*b* values.

22. An article as recited in claim 21, wherein said polymer sheet layer of said indicator section is composed of a linear-low-density-polyethylene material.

23. An absorbent article as recited in claim 21, wherein said indicator section provides a Contrast Ratio of at least about 2.

24. An article as recited in claim 21, wherein said indicator section provides a Contrast Ratio of at least about 3.

25. An absorbent article as recited in claim 21, wherein said polymer sheet layer includes a core layer sandwiched between skin layers, and said core layer includes a linear-low-density-polyethylene material.

26. An absorbent article having a front waistband portion, a back waistband portion and an intermediate portion, said article comprising:

a flexible and readily conformable backsheet member;

a liquid permeable topsheet layer;

an absorbent body having a retention portion and sandwiched between said backsheet member and said topsheet layer; and a wetness indicator for visually showing a presence of liquid in selected regions of said article, said wetness indicator including;

at least one indicator section of said backsheet member which includes a backsheet material having a polymer sheet backsheet member, said polymer sheet including a core layer sandwiched between skin layers, said core layer including a linear-low-density-polyethylene material, said indicator section of said backsheet member including a plurality of translucent windows which are arranged in an area pattern and are formed by a thermal treatment of said polymer sheet layer, said indicator section having a first appearance when portions of the article at the translucent windows are dry and having a visually different second appearance when portions of the article at the translucent windows are wetted with water.

27. An absorbent article having a front waistband portion, a back waistband portion and an intermediate portion, said article comprising:

a flexible and readily conformable backsheet member;

a liquid permeable topsheet layer;

an absorbent body having a retention portion sandwiched between said backsheet member and said topsheet layer; and a wetness indicator for visually showing a presence of liquid in selected regions of said article, said wetness indicator including;

at least one indicator section of said backsheet member which includes a backsheet laminate material having a fibrous nonwoven web attached to a polymer sheet layer, said polymer sheet layer including a core layer sandwiched between skin layers, said core layer including a linear-low-density-polyethylene material, said indicator section of said backsheet member including a plurality of translucent windows which are arranged in an area pattern and are formed by a selected thermal bonding of said fibrous nonwoven web to said polymer sheet layer in said backsheet laminate material; and a layer of contrast material attached to said article at an operative location which is interposed between an intended wearer of the article and said indicator section of the backsheet member, said contrast layer having a first appearance through said translucent windows when said contrast material is dry, and having a visually different second appearance through said translucent windows when said contrast material is wetted with water.

28. An absorbent article as recited in claim 27, wherein at least one said skin layer is compatible with said nonwoven layer and said core layer, and has been attached to said fibrous nonwoven layer upon an application of heat and pressure.

29. An absorbent article as recited in claim 28, wherein said at least one skin layer provides a meltable intermediary between said core layer and said fibrous nonwoven layer.

30. An absorbent article having a front waistband portion, a back waistband portion and an intermediate portion, said article comprising:

a flexible and readily conformable backsheet member;

a liquid permeable topsheet layer;

an absorbent body having a retention portion and sandwiched between said backsheet member and said topsheet layer; and a wetness indicator for visually showing a presence of liquid in selected regions of said article, said wetness indicator including;

at least one indicator section of said backsheet member which includes a backsheet material having a polymer sheet layer composed of a linear-low-density-polyethylene material, said indicator section of said backsheet member including a plurality of translucent windows which are arranged in an area pattern and are formed by a thermal treatment of said polymer sheet layer, said indicator section having a first appearance when portions of the article at the translucent windows are dry and having a visually different second appearance when portions of the article at the translucent windows are wetted with waters and said indicator section providing a Contrast Ratio of at least about 1.3, as determined with Hunter L*a*b* values.

31. An absorbent article as recited in claim 30, wherein said indicator section provides a Contrast Ratio of at least about 2.

32. An absorbent article as recited in claim 30, wherein said indicator section provides a Contrast Ratio of at least about 3.

33. An absorbent article as recited in claim 30, wherein said polymer sheet layer includes a core layer sandwiched between skin layers, and said core layer includes said linear-low-density-polyethylene material.

* * * * *

UNITED STATES PATENT AND TRADEMARK OFFICE
CERTIFICATE OF CORRECTION

PATENT NO. : 6,075,178  
DATED : June 13, 2000  
INVENTOR(S) : Hoa La Wilhelm et al.

Page 1 of 1

It is certified that error appears in the above-identified patent and that said Letters Patent is hereby corrected as shown below:

Title page,
Item [56], please add -- A1 -- after "WO 97/48358".

Column 1,
Line 7, delete "non", and substitute -- name --, also insert one space after the word "Wilhelm".

Column 2,
Line 48, delete "al", and substitute -- at --.

Column 6,
Line 18, delete "T", and substitute -- I --.

Column 7,
Line 48, delete "T", and substitute -- I --.

Column 12,
Line 28, delete "1.4", and substitute -- 1:4 --.

Column 25,
Line 18, delete "all.", and substitute -- al. --

Column 29,
Line 21, delete "13", and substitute -- 8 --.

Column 36,
Line 31, delete "I", and substitute -- 1 --.

Signed and Sealed this

Fifth Day of February, 2002

*Attest:*

JAMES E. ROGAN  
*Attesting Officer*     *Director of the United States Patent and Trademark Office*